US008394593B2

(12) United States Patent
Robinson et al.

(10) Patent No.: US 8,394,593 B2
(45) Date of Patent: Mar. 12, 2013

(54) USE OF AN IL-12 RECEPTOR SPLICE VARIANT AND MOLECULAR ASSAY TO QUANTIFY EXPRESSION THEREOF

(75) Inventors: Richard T. Robinson, Milwaukee, WI (US); Andrea M. Cooper, Saranac Lake, NY (US)

(73) Assignee: Trudeau Institute, Saranac Lake, NY (US)

( * ) Notice: Subject to any disclaimer, the term of this patent is extended or adjusted under 35 U.S.C. 154(b) by 0 days.

(21) Appl. No.: 13/022,224

(22) Filed: Feb. 7, 2011

(65) Prior Publication Data

US 2011/0256158 A1    Oct. 20, 2011

Related U.S. Application Data

(60) Provisional application No. 61/304,025, filed on Feb. 12, 2010.

(51) Int. Cl.
*C12Q 1/68* (2006.01)
*C07H 21/04* (2006.01)

(52) U.S. Cl. ............... 435/6.17; 435/6.11; 435/6.12; 536/24.31; 536/24.33

(58) Field of Classification Search ............ None
See application file for complete search history.

(56) References Cited

U.S. PATENT DOCUMENTS 7,482,117 B2 * 1/2009 Cargill et al. ............ 435/6.14

OTHER PUBLICATIONS

Kafert et al. 1999. Anal. Biochem. 269:210-213.*
van de Vosse et al. 2003. Immunogenetics 54:817-829.*
Grahn et al. 2001. Glycoconjugate J. 18:759-767.*
Grohmann et al. 1998. Immunity. 9:315-323.*
Allavena, et al., "Interleukin-12 is chemotactic for natural killer cells and stimulates their interaction with vascular endothelium." *Blood* 84(7): 2261-2268 (1994).
Altare, et al., "Impairment of mycobacterial immunity in human interleukin-12 receptor deficiency." *Science* 280:1432-1435 (1998).
Capon, et al., "Sequence variants in the genes for the interleukin-23 receptor (IL23R) and its ligand (IL12B) confer protection against psoriasis." *Hum Genet.* 122(2):201-6 (2007).
Carthew, "Gene silencing by double-stranded RNA." *Curr. Opin. Cell Biol.* 13(2):244-248 (2001).
Chua, et al., "Expression cloning of a human IL-12 receptor component. A new member of the cytokine receptor superfamily with strong homology to gp130." *J Immunology* 153(1):128-36 (1994).
Chua, et al., "Cloning and characterization of a mouse IL-12 receptor-beta component." *J Immunology* 155:4286-4299 (1995).
Cooper, et al., "Cell-mediated immune responses in tuberculosis." *Annu Rev Immunol*, 27:393-422 (2009).
Dasgupta, et al., "Generation of functional blocking monoclonal antibodies against mouse interleukin-12 p40 homodimer and monomer." *Hybridoma (Larchmt)* 27:141-151 (2008).

De Jong, et al., "Severe mycobacterial and *Salmonella* infections in interleukin-12 receptor-deficient patients." *Science* 280:1435-1438 (1998).
Filipe-Santos, et al., "Inborn errors of IL-12/23- and IFN-gamma-mediated immunity: molecular, cellular, and clinical features." *Semin Immunol*, 18:347-361 (2006).
Fortin, et al., "Host genetics of mycobacterial diseases in mice and men: forward genetic studies of BCG-osis and tuberculosis." *Annu Rev Genomics Hum Genet*, 8:163-192 (2007).
Gallegos, et al., "Delayed protection by ESAT-6-specific effector CD4+ T cells after airborne M. tuberculosis infection." *J Exp Med*, 205:2359-2368 (2008).
Grohmann, et al., "IL-12 acts directly on DC to promote nuclear localization of NF-kappaB and primes DC for IL-12 production." *Immunity* 9:315-323 (1998).
Jang, et al., "Distinct chemokine and cytokine gene expression pattern of murine dendritic cells and macrophages in response to *Mycobacterium tuberculosis* infection." *J Leukoc Biol*, 84:12641270 (2008).
Johnson, et al., "Genome-wide survey of human alternative pre-mRNA splicing with exon junction microarrays." *Science*, 302:2141-2144 (2003).
Jung, et al., "In vivo depletion of CD11c+ dendritic cells abrogates priming of CD8+ T cells by exogenous cell-associated antigens." *Immunity* 17(2):211-20 (2002).
Khader, et al., "Interleukin 12p40 is required for dendritic cell migration and T cell priming after *Mycobacterium tuberculosis* infection." *J Exp Med*, 203:1805-1815 (2006).
Khader, et al., "IL-23 and IL-17 in the establishment of protective pulmonary CD4+ T cell responses after vaccination and during *Mycobacterium tuberculosis* challenge." Nat Immunol, 8:369-377 (2007).
Lambrecht, "Lung dendritic cells: targets for therapy in allergic disease." *Curr Mol Med*, 8:393-400 (2008).
Levine, "Mechanisms of soluble cytokine receptor generation." *J Immunol*, 173, 5343-5348 (2004).
Lynch, Consequences of regulated pre-mRNA splicing in the immune system. *Nat Rev Immunol*, 4:931-940 (2004).
Magram, et al., "IL-12-deficient mice are defective in IFN gamma production and type 1 cytokine responses." *Immunity*, 4:471-481 (1996).
Mccormick, et al., "Mucosally delivered dendritic cells activate T cells independently of IL-12 and endogenous APCs." *J Immunol*, 181:2356-2367 (2008).
Mizushima, et al., "pEF-BOS, a powerful mammalian expression vector." *Nucleic Acids Res*, 18:5322 (1990).
Mogues, et al., "The relative importance of T cell subsets in immunity and immunopathology of airborne *Mycobacterium tuberculosis* infection in mice." *J Exp Med*, 193:271-280 (2001).
Nagayama, et al., "IL-12 responsiveness and expression of IL-12 receptor in human peripheral blood monocyte-derived dendritic cells." *J Immunol*, 165:59-66 (2000).

(Continued)

*Primary Examiner* — Shulamith H Shafer

(74) *Attorney, Agent, or Firm* — Medlen & Carroll, LLP

(57) ABSTRACT

The present invention describes compositions for both diagnostic and therapeutic applications. In one embodiment, the present invention contemplates a vaccine formulation comprising an antigen and IL12Rβ1 isoform 2. In some embodiments, this invention relates to a method of quantifying the ratio of IL12Rβ1 transcript and a splice variant thereof in a sample, including but not limited to at the cDNA level. In other embodiments, this invention relates to a method of augmenting an immune response by administering, inhibiting and/or inducing IL12Rβ1 isoform 2.

15 Claims, 18 Drawing Sheets

OTHER PUBLICATIONS

Oppmann, et al.," Novel p19 protein engages IL-12p40 to form a cytokine, IL-23, with biological activities similar as well as distinct from IL-12." *Immunity*, 13:715-725 (2000).

Pannetier, et al., "The sizes of the CDR3 hypervariable regions of the murine T-cell receptor beta chains vary as a function of the recombined germ-line segments." *Proc Natl Acad Sci U S A*, 90:4319-4323 (1993).

Parham, et al., "A receptor for the heterodimeric cytokine IL-23 is composed of IL-12Rbeta1 and a novel cytokine receptor subunit, IL-23R." *J Immunol*, 168:5699-5708 (2002).

Ponsaerts, et al., "mRNA-electroporated mature dendritic cells retain transgene expression, phenotypical properties and stimulatory capacity after cryopreservation." *Leukemia*, 16, 1324-1330 (2002).

Presky, et al., "A functional interleukin 12 receptor complex is composed of two beta-type cytokine receptor subunits." *Proc Natl Acad Sci U S A*, 93:14002-14007 (1996).

Presky, et al., "Analysis of the multiple interactions between IL-12 and the high affinity IL-12 receptor complex." *J Immunol*, 160:2174-2179 (1998).

Reiley, et al., "ESAT-6-specific CD4 T cell responses to aerosol *Mycobacterium tuberculosis* infection are initiated in the mediastinal lymph nodes." *Proc Natl Acad Sci U S A*, 105:10961-10966 (2008).

Reinhardt, et al., "Visualization of IL-12/23p40 in vivo reveals immunostimulatory dendritic cell migrants that promote Th1 differentiation." *J Immunol*, 177:1618-1627 (2006).

Robinson, et al., "*Yersinia pestis* evades TLR4-dependent induction of IL-12(p40)2 by dendritic cells and subsequent cell migration." *J Immunol*, 181:5560-5567 (2008).

Taha, et al., "Increased expression of IL-12 receptor mRNA in active pulmonary tuberculosis and sarcoidosis." *Am J Respir Crit Care Med*, 160:1119-1123 (1999).

Takahashi, et al., "Association of the IL12RB1 promoter polymorphisms with increased risk of atopic dermatitis and other allergic phenotypes." *Hum Mol Genet*, 14:3149-3159 (2005).

Takahashi, et al., "Association of the IL12RB1 promoter polymorphisms with increased risk of atopic dermatitis and other allergic phenotypes." *Hum Mol Genet*, 14:3149-3159 (2005)—Suppl data.

Tian, et al., "In vivo depletion of CD11c+ cells delays the CD4+ T cell response to *Mycobacterium tuberculosis* and exacerbates the outcome of infection." *J Immunol*, 175:3268-3272 (2005).

van de Vosse, et al., "Genetic variations in the interleukin-12/interleukin-23 receptor (beta1) chain, and implications for IL-12 and IL-23 receptor structure and function." *Immunogenetics* 54:817 (2003).

Van Rietschoten, et al., "Genomic organization of the human interleukin-12 receptor beta2-chain gene." *Immunogenetics*, 51:30-36 (2000).

Wang, et al., "Characterization of mouse interleukin-12 p40 homodimer binding to the interleukin-12 receptor subunits." *Eur J Immunol*, 29:2007-2013 (1999).

Winslow, et al., "Early T-cell responses in tuberculosis immunity." *Immunol Rev*, 225, 284-299 (2008).

Winter and Milstein, "Man-made antibodies." *Nature*, 349:293-299 (1991).

Wolf, et al., "*Mycobacterium tuberculosis* infects dendritic cells with high frequency and impairs their function in vivo." *J Immunol*, 179:2509-2519 (2007).

Wolf, et al., "*Mycobacterium tuberculosis* infects dendritic cells with high frequency and impairs their function in vivo." *J Immunol*, 179:2509-2519 (2007)—Suppl FigS1.

Wolf, et al., "*Mycobacterium tuberculosis* infects dendritic cells with high frequency and impairs their function in vivo." *J Immunol*, 179:2509-2519 (2007)—Suppl FigS2.

Wolf, et al., "*Mycobacterium tuberculosis* infects dendritic cells with high frequency and impairs their function in vivo." *J Immunol*, 179:2509-2519 (2007)—Suppl FigS3.

Wolf, et al., "Initiation of the adaptive immune response to *Mycobacterium tuberculosis* depends on antigen production in the local lymph node, not the lungs." *J Exp Med*, 205:105-115 (2008).

Wu, et al., "Characterization of IL-12 receptor beta1 chain (IL-12Rbeta1)-deficient mice: IL-12Rbeta1 is an essential component of the functional mouse IL-12 receptor." *J Immunol*, 159:1658-1665 (1997).

Wu, et al., "IL-12 receptor beta 2 (IL-12R beta 2)-deficient mice are defective in IL-12-mediated signaling despite the presence of high affinity IL-12 binding sites." *J Immunol*, 165:6221-622 (2000).

Zhang, et al., "Role of IL-12 receptor beta 1 in regulation of T cell response by APC in experimental autoimmune encephalomyelitis." *J Immunol*, 171:4485-4492 (2003).

\* cited by examiner

US 8,394,593 B2

USE OF AN IL-12 RECEPTOR SPLICE VARIANT AND MOLECULAR ASSAY TO QUANTIFY EXPRESSION THEREOF

This application claims the benefit of priority to Provisional Application U.S. Ser. No. 61/304,025, which was filed on Feb. 12, 2010, the disclosures of which are incorporated herein by reference.

This invention was made with government support under grant number R01 AI067723 awarded by the National Institutes of Health. The government has certain rights in the invention.

FIELD OF THE INVENTION

The present invention relates generally to methods and compositions for both diagnostic and therapeutic applications. In one embodiment, the present invention contemplates a vaccine formulation comprising an antigen and the IL12 Receptor Beta 1 (IL12Rβ1) isoform 2. In some embodiments this invention relates to a method of quantifying the ratio of IL12Rβ1 cDNA and a splice variant thereof in a sample. In other embodiments, this invention relates to a method of augmenting an immune response by administering, inhibiting and/or inducing the IL12Rβ1 isoform 2.

BACKGROUND

Induction of type-1 cell-mediated immune responses is an important component of a host organism's response to a variety of bacterial, fungal and viral pathogens. The release of inflammatory mediators, including pro-inflammatory cytokines, is common component of this immune reaction. In some instances it is desirable to enhance the cell-mediated immune response, as for example along with or following vaccination to a desired antigen. In other instances it is desirable to reduce the cell-mediated immune response, for example to avoid cell and/or tissue damage due to excessive inflammation. What is needed is the ability to augment the course of the type-1 mediated immune response depending on the circumstances facing an individual patient.

SUMMARY OF THE INVENTION

The present invention relates generally to methods and compositions for both diagnostic and therapeutic applications. In one embodiment, the present invention contemplates a vaccine formulation comprising an antigen and the IL12Rβ1 isoform 2. In some embodiments this invention relates to a method of quantifying the ratio of IL12Rβ1 cDNA and a splice variant thereof in a sample. In other embodiments, this invention relates to a method of augmenting an immune response by administering, inhibiting and/or inducing the IL12Rβ1 isoform 2.

In some embodiments, the present invention relates generally to a vaccine formulation comprising an antigen and the IL12Rβ1 isoform 2.

In some embodiments, the present invention relates generally to a method for quantifying a transcript and a splice variant of said transcript for diagnostic purposes. In one embodiment, the method comprises providing a sample that comprises cDNA molecules encoding IL12Rβ1 isoform 1 and IL12Rβ1 isoform 2, a PCR primer set flanking the trans-membrane-encoding region of the cDNA molecules, and a fluorescent-conjugated primer, amplifying the cDNAs with the PCR primer set, labeling the products of the PCR amplification with the fluorescent-conjugated primer and detecting the labeled PCR products. In some embodiments, the nucleotide sequence of the forward PCR primer is SEQ ID NO:1. In some embodiments, the nucleotide sequence of the reverse PCR primer is SEQ ID NO:2. In other embodiments, detecting the labeled PCR products further comprises detecting the ratio of transcript encoding IL12Rβ1 isoform 1 to splice variant encoding IL12Rβ1 isoform 2. In further embodiments, the sample is isolated from a cell. In still further embodiments, the cell is a dendritic cell. In some embodiments, the cell has been exposed to a pathogen. In other embodiments, the pathogen is *Mycobacterium tuberculosis*.

In some embodiments, the present invention relates generally to a method of augmenting an immune response comprising, providing a subject and a peptide isoform of an IL12Rβ1 splice variant, and administering said peptide isoform to said subject. In some embodiments, the peptide isoform is the IL12Rβ1 isoform 2. In some embodiments, the peptide isoform is a fragment of the IL12Rβ1 isoform 2. In other embodiments, administering the splice variant enhances a type-1 cellular immune response in the subject. In other embodiments, the splice variant is administered concomitant with a vaccination. In still other embodiments, the splice variant is administered concomitant with an immunotherapy. In other embodiments, at least a fragment of said peptide isoform is administered to said subject.

In some embodiments, the present invention relates generally to a method of augmenting an immune response, comprising providing a subject and an inhibitor of a peptide isoform of an IL12Rβ1 splice variant, and administering the inhibitor to the subject. In some embodiments, the peptide isoform is IL12Rβ1 isoform 2. In some embodiments, the peptide isoform is a fragment of the IL12Rβ1 isoform 2. In other embodiments, the splice variant is administered concomitant with a vaccination. In other embodiments, the inhibitor comprises a monoclonal or polyclonal antibody specific for the IL12Rβ1 isoform 2. In further embodiments, the inhibitor comprises a siRNA molecule specific for the splice variant encoding the IL12Rβ1 isoform 2. In still further embodiments, administering the inhibitor limits a type-1 cellular immune response in the subject. In some embodiments, administering the inhibitor limits an inflammatory immune response in said subject. In other embodiments, the inflammatory response is an IL12 dominated immune response.

In some embodiments, the present invention relates generally to a method of augmenting an immune response comprising, providing a subject and a compound capable of inducing expression of a peptide isoform of an IL12Rβ1 splice variant, and administering the compound to the subject such that expression of the peptide isoform is induced. In some embodiments, the peptide isoform is the IL12Rβ1 isoform 2. In some embodiments, the peptide isoform is a fragment of the IL12Rβ1 isoform 2. In some embodiments, the compound is a subunit of *Mycobacterium tuberculosis*. In some embodiments, the compound is a glycolipid molecule of *Mycobacterium tuberculosis*. In other embodiments, inducing expression of the splice variant enhances a type-1 cellular immune response in the subject. In other embodiments, the splice variant is induced concomitant with a vaccination. In still other embodiments, the splice variant is induced concomitant with an immunotherapy.

In some embodiments, the present invention relates generally to a primer having the nucleotide sequence of SEQ ID NO: 1. (5'-ACACTCTGGGTGGAATCCTG-3' [Forward])

In some embodiments, the present invention relates generally to a primer set comprising a first primer having the nucleotide sequence of SEQ ID NO: 1 and a second primer having the nucleotide sequence of SEQ ID NO: 2. (5'GC-CAACTTGGACACCTTGAT-3' [Reverse])

In some embodiments, the present invention relates generally to a kit comprising a primer set comprising a first primer having the nucleotide sequence of SEQ ID NO: 1 and a second primer having the nucleotide sequence of SEQ ID NO: 2.

In some embodiments, the present invention relates generally to a vaccine formulation comprising an antigen and a peptide isoform of the splice variant IL12Rβ1ΔTM.

In some embodiments, the present invention relates generally to a method for quantifying a transcript and a splice variant of said transcript for diagnostic purposes. In one embodiment, the method comprises providing a sample that comprises IL12Rβ1 and IL12Rβ1ΔTM cDNA molecules, a PCR primer set flanking the transmembrane-encoding region of the cDNA molecules, and a fluorescent-conjugated primer, amplifying the cDNAs with the PCR primer set, labeling the products of the PCR amplification with the fluorescent-conjugated primer and detecting the labeled PCR products. In some embodiments, detecting the labeled PCR products further comprises detecting the ratio of IL12Rβ1 to IL12Rβ1ΔTM. In further embodiments, the sample is isolated from a cell. In still further embodiments, the cell is a dendritic cell. In some embodiments, the cell has been exposed to a pathogen. In other embodiments, the pathogen is *Mycobacterium tuberculosis*.

In some embodiments, the present invention relates generally to a method of augmenting an immune response comprising, providing a subject and a peptide isoform of an IL12Rβ1 splice variant, and administering said peptide isoform to said subject. In some embodiments, the peptide isoform is the IL12Rβ1 splice variant IL12Rβ1ΔTM. In some embodiments, the peptide isoform is a fragment of the IL12Rβ1 splice variant IL12Rβ1ΔTM. In other embodiments, administering the splice variant enhances a type-1 cellular immune response in the subject. In other embodiments, the splice variant is administered concomitant with a vaccination. In still other embodiments, the splice variant is administered concomitant with an immunotherapy. In other embodiments, a fragment of said peptide isoform is administered to said subject.

In some embodiments, the present invention relates generally to a method of augmenting an immune response, comprising providing a subject and an inhibitor of a peptide isoform of an IL12Rβ1 splice variant, and administering the inhibitor to the subject. In some embodiments, the peptide isoform is the IL12Rβ1 splice variant IL12Rβ1ΔTM. In some embodiments, the peptide isoform is a fragment of the IL12Rβ1 splice variant IL12Rβ1ΔTM. In other embodiments, the splice variant is administered concomitant with a vaccination. In other embodiments, the inhibitor comprises a monoclonal or polyclonal antibody specific for the peptide isoform IL12Rβ1ΔTM. In further embodiments, the inhibitor comprises a siRNA molecule specific for the mRNA encoding the peptide isoform IL12Rβ1ΔTM. In still further embodiments, administering the inhibitor limits a type-1 cellular immune response in the subject. In some embodiments, administering the inhibitor limits an inflammatory immune response in said subject. In other embodiments, the inflammatory response is an IL12 dominated immune response.

In some embodiments, the present invention relates generally to a method of augmenting an immune response comprising, providing a subject and a compound capable of inducing expression of a peptide isoform of an IL12Rβ1 splice variant, and administering the compound to the subject such that expression of the peptide isoform is induced. In some embodiments, the peptide isoform is the splice variant IL12Rβ1ΔTM. In some embodiments, the peptide isoform is a fragment of the IL12Rβ1 splice variant IL12Rβ1ΔTM. In some embodiments, the compound is a subunit of *Mycobacterium tuberculosis*. In some embodiments, the compound is a glycolipid molecule of *Mycobacterium tuberculosis*. In other embodiments, inducing expression of the splice variant enhances a type-1 cellular immune response in the subject. In other embodiments, the splice variant is induced concomitant with a vaccination. In still other embodiments, the splice variant is induced concomitant with an immunotherapy.

DEFINITIONS

To facilitate the understanding of this invention a number of terms are defined below. Terms defined herein (unless otherwise specified) have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, terms defined in the singular are intended to include those terms defined in the plural and vice versa.

As used herein, the terms "patient" and "subject" refer to a human or animal who is ill or who is undergoing treatment for disease, but does not necessarily need to be hospitalized. For example, out-patients, persons in nursing homes are "patients".

As used herein, the term "concomitant" refers to existing, occurring or accompanying together or along with something else, sometimes (but not always) in a lesser way (e.g. a peptide of IL12Rβ1 isoform 2 may be administered concomitant with a vaccine formulation such that the immunizing effects of the vaccine are enhanced).

As used herein, the term "nucleic acid" refers to a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a nucleic acid at which a new linkage would be to a 5' pentose carbon is its 5' terminal nucleotide (by convention sequences are written, from right to left, in the 5' to 3' direction). The end of a nucleic acid at which a new linkage would be to a 3' pentose carbon is its 3' terminal nucleotide. A terminal nucleotide, as used herein, is the nucleotide at the end position of the 3'- or 5'-terminus. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, the term "oligonucleotide" refers to a short polynucleotide or a portion of a polynucleotide comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The word "oligo" is sometimes used in place of the word "oligonucleotide".

As used herein, the term "an oligonucleotide having a nucleotide sequence encoding a gene" or "a nucleic acid sequence encoding" a specified polypeptide refers to a nucleic acid sequence comprising the coding region of a gene or in other words the nucleic acid sequence that encodes a gene product. The coding region may be present in cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "gene" refers to a nucleic acid (for example, DNA or RNA) sequence that comprises coding sequences necessary for the production of RNA, or a polypeptide or its precursor. A functional polypeptide can be encoded by a full-length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene. The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "coding region" refers to the nucleotide sequences that encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets that specify stop codons (i.e., TAA, TAG, TGA).

As used herein, the term the terms "peptide", "peptide sequence", "amino acid sequence", "polypeptide", and "polypeptide sequence" are used interchangeably herein to refer to at least two amino acids or amino acid analogs that are covalently linked by a peptide bond or an analog of a peptide bond. The term peptide includes oligomers and polymers of amino acids or amino acid analogs. The term peptide also includes molecules that are commonly referred to as peptides, which generally contain from about two (2) to about twenty (20) amino acids. The term peptide also includes molecules that are commonly referred to as polypeptides, which generally contain from about twenty (20) to about fifty amino acids (50). The term peptide also includes molecules that are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide that is produced by artificial means in vitro.

As used herein, the term "alternative splicing" refers to the process by which the exons of the RNA produced by transcription of a gene (a primary gene transcript or pre-mRNA) are reconnected in multiple ways during RNA splicing. The resulting different mRNAs, referred to as "splice variants" or "alternative splice variants", may be translated into different protein isoforms; thus a single gene may code for multiple proteins. In eukaryotes, alternative splicing greatly increases the diversity of proteins that can be encoded by the genome. In humans, for example, over 80% of genes are alternatively spliced. There are numerous modes of alternative splicing, such as exon skipping in which a particular exon may be included in an mRNA under certain conditions (or in certain tissues) and omitted from the mRNA under other conditions. For example, IL12Rβ1ΔTM mRNA is an alternative splice variant of the IL-12 Receptor Beta 1 (IL12Rβ1) gene involved in IL-12 signaling pathways. Using PCR primer sets that flank (i.e. hybridize to regions 3' and 5') an alternative splice site (i.e. splice junction) it is possible to amplify cDNA molecules representing both the spliced and unspliced RNA molecules. PCR amplification products produced from the spliced cDNA template will be smaller than those produced from the unspliced cDNA template.

As used herein, the term "polymerase chain reaction" ("PCR") refers to the method of Mullis as provided for in U.S. Pat. Nos. 4,683,195, 4,683,202, and 4,965,188, incorporated herein by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product", "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "real time PCR" or "Taqman real time PCR" refers to a modified PCR that allows simultaneous amplification and quantification of a specific target DNA or cDNA molecule using sequence-specific RNA or DNA-based reporter probes. The reported probe only hybridizes to DNA or cDNA targets that contain the probe sequence, thereby significantly increasing specificity and allowing quantification even in the presence of non-specific amplification. The reported probe typically bears a fluorescent reporter at one end of the DNA or RNA molecule and a quencher of that fluorescence at the opposite end of the molecule. The quencher molecule blocks the fluorescence emitted by the fluorophore when excited by the PCR cycler's light source via FRET (Fluorescence Resonance Energy Transfer). As long as the fluorophore and the quencher are in proximity, quenching inhibits any fluorescence signals. As the Taq polymerase extends the primer and synthesizes the nascent strand, the 5' to 3' exonuclease activity of the Taq polymerase degrades the probe that has annealed to the template. Degradation of the probe releases the fluorophore such that it is no longer in close proximity to the quencher, thus relieving the quenching effect and allowing fluorescence of the fluorophore. Fluorescence detected in the real-time PCR thermal cycler is therefore directly proportional to the fluorophore released and the amount of DNA template present in the PCR. The product targeted by the reporter probe at each PCR cycle therefore causes a proportional increase in fluorescence due to the breakdown of the probe and release of the reporter. TaqMan probes may, for example, consist of a fluorophore covalently attached to the 5'-end of an oligonucleotide probe and a quencher at its 3'-end. Several different fluorophores are available, such as 6-carboxyfluorescein (i.e. FAM) or tetrachlorofluorescin (i.e. TET). Likewise, several different quenchers are also available, such as tetramethylrhodamine (i.e. TAMRA) or dihydrocyclopyrroloindole tripeptide minor groove binder (i.e. MGB). This potentially allows for multiplex assays for several genes in the same reaction by using specific probes with different colored labels, provided that all genes are amplified with similar efficiency.

As used herein, an "aerosol" is defined as a suspension of liquid or solid particles of a substance (or substances) in a gas. The present invention contemplates the use of both atomizers and nebulizers of various types. An "atomizer" is an aerosol generator without a baffle, whereas a "nebulizer" uses a baffle to produce smaller particles.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA, completely or partially, as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2): 244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include (but are not limited to) linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

As used herein, the term "antibody" or "antibodies" refers to globular proteins ("immunoglobulins") produced by cells of the immune system to identify and neutralize foreign antigens. "Monoclonal antibodies" (mAb) are antibodies that recognize a specific antigenic epitope (i.e. monospecific) because they are derived from clones of a single hybridoma. Hybridomas are cells engineered to produce a desired mAb antibody in large amounts. Briefly, B-cells are removed from the spleen of an animal that has been challenged with the desired antigen. These B-cells are then fused with myeloma tumor cells that can grow indefinitely (i.e. immortal) in culture. Since the fused cell or hybridoma is also immortal it will multiply rapidly and indefinitely to produce large amounts of the desired mAb (Winter and Milstein, Nature, 349, 293-299, 1991). "Polyclonal antibodies" (pAb) are a mixture of antibodies that recognize multiple epitopes of a specific antigen. Polyclonal antibodies are produced by immunizing an animal (i.e. mouse, rabbit, goat, horse, sheep etc.) with a desired antigen to induce B-lymphocytes to produce antibodies to multiple epitopes of that antigen. These antibodies can then be isolated from the animal's blood using well-known methods, such as column chromatography.

As used herein, the term "lymphocyte" refers to white blood cells that include B lymphocytes (B cells) and T lymphocytes (T cells). Individual B cells and T cells specifically recognize a single antigenic epitope and also recognize the body's own (self) tissues as different from non-self tissues. After B cells and T cells are formed, a small population will multiply and provide "memory" for the immune system. This allows the immune system to respond faster and more efficiently the next time you are exposed to the same antigen.

As used herein, the terms "inhibit", "inhibition", "inhibitor" or "suppress" and grammatical equivalents thereof, refer to the act of diminishing, suppressing, alleviating, limiting, eliminating, preventing, blocking and/or decreasing an action and/or function; as for example the inhibition of a chemical reaction or biological process. As used herein, it is not necessary that there be complete inhibition, it is sufficient for there to be some inhibition. For example, a compound that inhibits cancer may kill all cancerous cells or prevent, arrest or slow further cancerous cell growth. These terms find use in both in vitro as well as in vivo systems.

As used herein, the terms "reduce" and "reduction" and grammatical equivalents thereof, means lowering, decreasing, or diminishing in degree, intensity, extent, and/or amount. As used herein, it is not necessary that there be complete reduction, it is sufficient for there to be some reduction.

As used herein, the terms "prevent" and "preventing" and grammatical equivalents thereof, indicates the hindrance of the recurrence, spread or onset of a disease or disorder. It is not intended that the present invention be limited to complete prevention. In some embodiments, the onset is delayed, or the severity of the disease or disorder is reduced.

As used herein, the terms "treat", "treating", "treatment" and grammatical equivalents thereof, refers to combating a disease or disorder, as for example in the management and care of a patient. "Treatment" is not limited to cases where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the term "downregulate" or "downregulation" refers to a decrease, relative to an appropriate control, in the amount of a given molecule, protein, gene product, or nucleic acid such as DNA or RNA due to exposure to or contact with an inhibitor.

As used herein, the terms "diagnose" "diagnosis" or "diagnosing" refers to the recognition of a disease by its signs and symptoms (e.g., resistance to conventional therapies), or genetic analysis, pathological analysis, histological analysis, and the like.

As used herein, a "diagnostic" is a compound or method that assists in the identification and characterization of a health or disease state. With regard to the present invention, it is contemplated that a method for determining the ratio of cDNA molecules encoding IL12Rβ1 isoform 1 to cDNA molecules encoding the splice variant IL12Rβ1 isoform 2 can be used as a diagnostic to evaluate the course of an immune response in a patient following an infection. For example, a patient infected with M. tuberculosis may be examined with such a diagnostic to determine whether a particular cytokine response has been stimulated as well as the relative levels of such cytokines.

As used herein, the term "cytokines" refers to a category of protein, peptide, or glycoprotein molecules secreted by specific cells of the immune system that carry signals between cells. Cytokines are a critical component of both the innate and adaptive immune response, and are often secreted by immune cells that have encountered a pathogen to activate and recruit additional immune cells to increase the system's response to the pathogen. Cytokines are typically released in the general region of the pathogen-infected cells such that responding immune cells arrive at that site of infection. Each individual cytokine has a matching cell-surface receptor. Upon binding of a cytokine to its cell-surface receptor a cascade of intracellular signaling events alters the cell's function. This includes the upregulation and/or downregulation of genes involved in the production of other cytokines, an increase expression of surface receptors for other molecules, or suppression of the cytokine itself by feedback inhibition. The effect of a particular cytokine on a given cell depends on the cytokine, its extracellular abundance, the presence and abundance of the complementary receptor on the cell surface, and downstream signals activated by receptor binding. Common cytokines include interleukins that are responsible for communication between white blood cells; chemokines that promote chemotaxis; and interferons that have anti-viral effects, such as shutting down protein synthesis in the host cell. Cytokines are characterized by considerable "redundancy", in that many cytokines appear to share similar functions.

Interleukin 12 (IL-12), also known as natural killer cell stimulatory factor (NKSF), T cell stimulatory factor, or cytotoxic lymphocyte maturation factor (CLMF), is a cytokine produced by dendritic cells (DCs), macrophages and B-cells in response to antigenic stimulation. IL-12 plays a central role in the initiation and regulation of cellular immune responses, including the differentiation of naive T cells into either Th1 or Th2 cells; a crucial in determining the type of reaction elicited in response to a particular pathogen. In addition to enhancing the cytotoxic activity of natural killer (NK) cells and $CD8^+$ cytotoxic T cells, IL-12 also stimulates the production of the cytokines interferon-gamma (IFN-γ) and tumor necrosis factor-alpha (TNF-α) by T and natural killer (NK) cells. IL-12 also has anti-angiogenic activity, which means it can block the formation of new blood vessels. It does this by increasing production of interferon gamma, which in turn increases the production of the inducible protein-10 (IP-10) chemokine. IP-10 then mediates this anti-angiogenic effect.

IL-12 binds to the heterodimeric IL-12 receptor (CD212) formed by IL12Rβ1 and IL12Rβ2 subunits. IL12Rβ2 plays a central role in IL-12 function, since it is found on activated T cells and is stimulated by cytokines that promote Th1 cell development and inhibited by those that promote Th2 cell development. Upon binding, IL12Rβ2 becomes tyrosine phosphorylated and provides binding sites for the Tyk2 and Jak2 kinases of the JAK-STAT pathway. These kinases are important in activating transcription factors (such as STAT4) involved in IL-12 signaling in T cells and NK cells. IL12 receptors are present on activated $CD4^+$ and $CD8^+$ positive T-cells and activated NK cells. IL-2 stimulates expression of the IL-12 receptors (IL12Rβ1 and IL12102), critical receptor proteins involved in IL-12 signaling in NK cells.

As used herein, the term "chemotaxis" or "chemotactic" refers to the movement or orientation of an organism or cell along a chemical concentration gradient either toward or away from the chemical stimulus. Movement towards a chemical stimulus is referred to as "positive chemotaxis", while movement away from a chemical stimulus is referred to as "negative chemotaxis". Chemotaxis requires cell motility (the ability to move spontaneously and independently), a specific receptor to recognize the chemical stimulus and a signaling pathway linking the receptor to the element(s) controlling the movement. Chemotaxis occurs in both single-cell and multi-cellular organisms. For example, bacteria exhibit chemotaxis when they move toward a source of nutrients (such as glucose) or move away from a poison (such as phenol). Multicellular organisms also utilize chemotaxis for numerous aspects of their development, including for example, the movement of sperm towards the egg during fertilization and the migration of neurons. A variety of immune cells (including granulocytes, monocytes and lymphocytes) are attracted to the site of infection by the release of chemotactic cytokines known as chemokines. NK cells, $CD4^+$ and $CD8^+$ T cells and polymorphonuclear cells (PMNs) have all been demonstrated to exhibit a positive chemotaxis response to IL-12 (Blood, 84(7): 2261-2268). In addition, subversion of the normal chemotaxis mechanism is a recognized factor in cancer metastasis.

As used herein, the term "T helper cell", "effector T cell" or "Th cell" refers to a sub-group of T lymphocytes involved in establishing and maximizing the capabilities of the immune system. While Th cells lack cytotoxic or phagocytic activity, they activate and direct other immune cells, such as B-cell antibody class switching and the activation and growth of cytotoxic T cells. Th cells are also involved in maximizing the activity of phagocytes such as macrophages. Mature Th cells express the surface protein CD4, and are therefore referred to as $CD4^+$ T cells. Th cells differentiate into two major subtypes of cells known as Type 1 (Th-1) and Type 2 (Th-2) helper cells, respectively.

As used herein, the term "cell-mediated immunity" refers to an immune response that does not involve antibodies or complement but rather involves the activation of macrophages, natural killer cells (NK), antigen-specific cytotoxic T-lymphocytes (T-cells), and the release of various cytokines in response to an antigen. Patterns of cytokine production by T cells are associated with different immunological responses, described as type-1 (Th-1) and type-2 (Th-2) responses. In some embodiments, the Th-1 response stimulates cell-mediated immunity by releasing cytokines such as IFN-γ, which increase the production of IL-12 by DCs and macrophages. In some embodiments, Il-12 also stimulates the production of IFN-γ in Th-1 cells by positive feedback. In further embodiments, IFN-γ also inhibits the production of cytokines associated with the Th-2 response, such as interleukin-4, thereby preserving the Th-1 response. In some embodiments, the Th-2 response stimulates the humoral immune system by promoting the proliferation of antibody producing B-cells. In some embodiments, the Th-2 response involves the release of cytokines such as IL-4 that further promotes the production of Th-2 cytokines. In other embodiments, the Th-2 response releases IL-10, which inhibits the production of Th-1 related cytokines such as interleukin-2 and IFN-γ in T helper cells and IL-12 in DCs and macrophages.

As used herein, the term "inflammatory response" refers to inflammation that occurs when tissues are injured by any number of causes, including for example, bacteria or virus infections, trauma, toxins and/or heat. Chemicals released by the damaged tissues (including cytokines, histamine, bradykinin and serotonin) cause blood vessels to leak fluid into the surrounding tissues resulting in local swelling. This helps isolate the foreign substance from further contact with body tissues. These chemicals also attract immune cells that function to clear microorganisms and dead or damaged cells by the process of phagocytosis.

As used herein, the term "dendritic cells" or "DCs" refers to immune cells that form part of the mammalian immune system. The main function of DCs is to functioning as "antigen-presenting cells" by processing foreign antigens and presenting antigenic epitopes on their surface to other cells of the immune system. DCs are present in small quantities in tissues that are in contact with the external environment, mainly the skin (where there is a specialized dendritic cell type called Langerhans cells) and the inner lining of the nose, lungs, stomach and intestines. DCs can also be found in an immature state in the blood. Once activated, they migrate to the lymphoid tissues where they interact with T cells and B cells to initiate the adaptive immune response. At certain development stages DCs grow branched projections (dendrites) that give the cell its name. In some embodiments, DCs can be differentiated into two sub-populations based on the expression of the cell surface marker CD11c. In some embodiments, $CD11c^+$ DCs produce IL12 and stimulate a Th1 response in lymphocytes, while $CD11c^-$ DCs synthesize little IL12 but are a major source of alpha-interferon and stimulate lymphocytes to produce Th2 cytokines.

As used herein, the term "vaccine", "vaccinate" or "vaccination" refers to the introduction of a small amount of an antigen into an organism in order to trigger an immune system that generates activated B cells and/or sensitized T cells. These cells recognize and eliminate the foreign antigen and also establish immune system "memory" such that future exposures to the antigen result in its rapid recognition and clearance. A variety of antigenic substances may be used for vaccination, including dead or inactivated (i.e. live attenuated) organisms or purified products derived therefrom. Vaccines can be used to prevent or ameliorate the effects of a future infection (i.e. prophylactic) or therapeutic, such as anti-cancer vaccine.

As used herein, the term "immunotherapy" refers to the treatment of a disease by inducing, enhancing or suppressing an immune response. Immunotherapies designed to elicit or amplify an immune response are classified as "activation immunotherapies", while those designed to reduce, suppress or direct an existing immune response are classified as "suppression immunotherapies". Immunotherapy agents may include a diverse array of recombinant, synthetic and natural preparations, including cytokines for example.

As used herein, the term "ELISPOT assay" or "Enzyme-Linked Immunosorbent Spot Assay" refers to a method for monitoring immune responses in humans and animals developed by Cecil Czerkinsky. The ELISPOT assay is a modified version of the ELISA immunoassay and was originally developed to enumerate B cells secreting antigen-specific antibodies. This assay has subsequently been adapted for various tasks, including the identification and enumeration of cytokine-producing cells at the single cell level. Briefly, the ELISPOT assay permits visualization of the secretory product of individual activated or responding cells. Each "spot" that develops in the assay represents a single reactive cell. Thus, the ELISPOT assay provides both qualitative (type of immune protein) and quantitative (number of responding cells) information. The sensitivity of the ELISPOT assay permits frequency analysis of rare cell populations (e.g., antigen-specific responses). This sensitivity is due in part to the ability to rapidly capture the product around the secreting cell before it is diluted in the supernatant, captured by receptors of adjacent cells, or degraded. This makes ELISPOT assays much more sensitive than conventional ELISA measurements. Limits of detection are below $1/100,000$ rendering the assay uniquely useful for monitoring antigen-specific responses, applicable to a wide range of areas of immunology research, including cancer, transplantation, infectious disease, and vaccine development.

As used herein, the term "*Mycobacterium tuberculosis*" refers to a pathogenic bacterial species in the genus *Mycobacterium* that is primarily a pathogen of mammalian respiratory systems and is the causative agent of most cases of tuberculosis. The cell surface of *M. tuberculosis* has a waxy coating composed primarily of mycolic acid, which renders the cell impervious to Gram staining.

As used herein, the term "fluorescence" refers to the emission of visible light by a substance that has absorbed light of a different wavelength. In some embodiments, fluorescence provides a non-destructive means of tracking and/or analyzing biological molecules based on the fluorescent emission at a specific frequency. Proteins (including antibodies), peptides, nucleic acid, oligonucleotides (including single stranded and double stranded primers) may be "labeled" with a variety of extrinsic fluorescent molecules referred to as fluorophores. Isothiocyanate derivatives of fluorescein, such as carboxyfluorescein, are an example of fluorophores that may be conjugated to proteins (such as antibodies for immunohistochemistry) or nucleic acids. In some embodiments, fluorescein may be conjugated to nucleoside triphosphates and incorporated into nucleic acid probes (such as "fluorescent-conjugated primers") for in situ hybridization. In some embodiments, a molecule that is conjugated to carboxyfluorescein is referred to as "FAM-labeled".

BRIEF DESCRIPTION OF THE FIGURES

For a more complete understanding of the features and advantages of the present invention, reference is now made to the detailed description of the invention along with the accompanying figures.

DETAILED DESCRIPTION OF THE INVENTION

Figure 1:
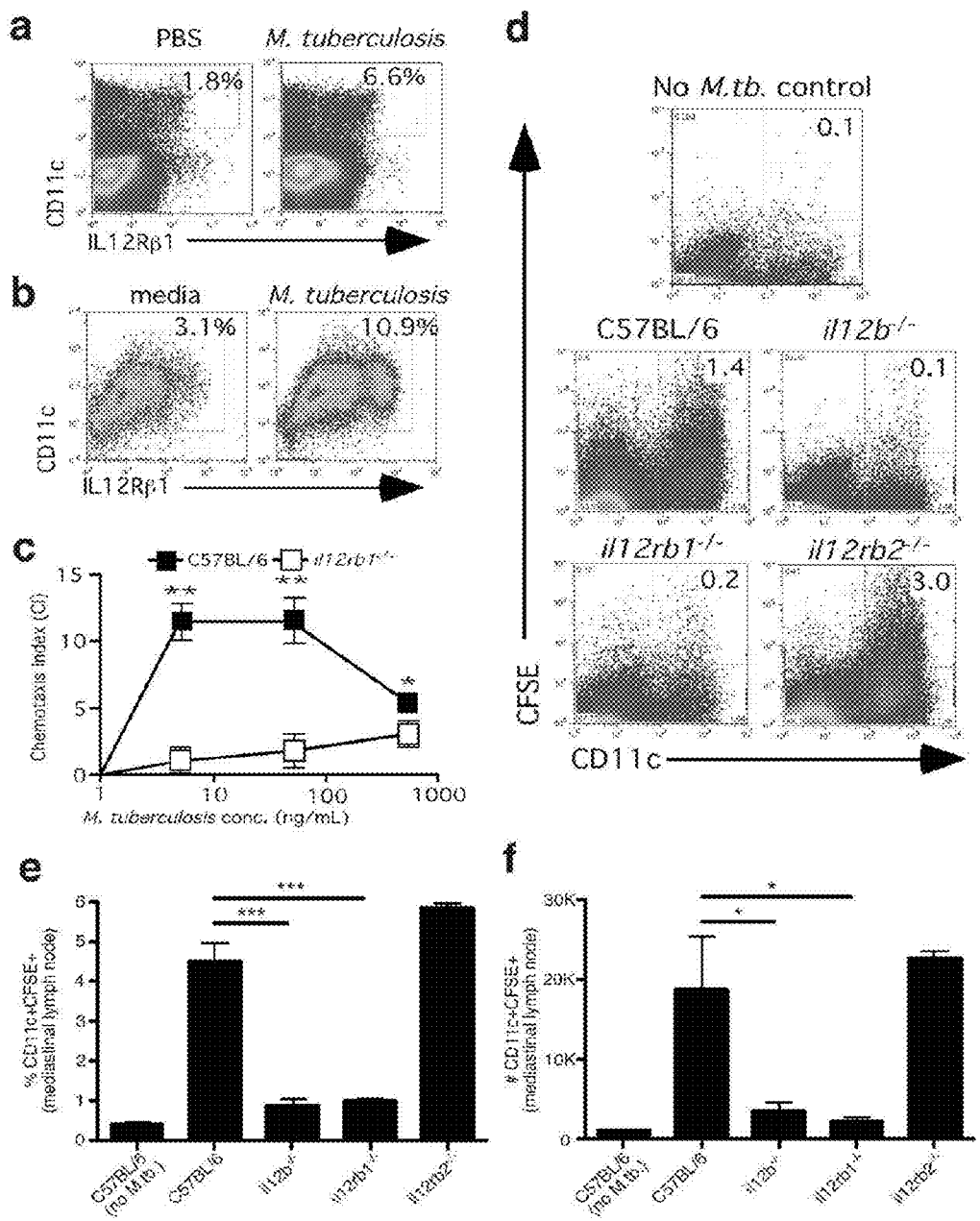
FIG. 1 depicts the role of IL12Rβ1 in *M. tuberculosis*-induced DC migration. (A) *M. tuberculosis* was instilled into the trachea of C57BL/6 mice and 3 hrs later the frequency of $CD11c^+IL12R\beta1^+$ cells in the lungs was determined. Dot plots are representative of four mice per condition; this experiment was performed twice. (B) C57BL/6 BMDCs were exposed to *M. tuberculosis* or media alone and 3 hrs later the frequency of $CD11c^+IL12R\beta1^+$ cells was determined. Dot plots represent the same BMDC preparation stimulated with either condition and are representative of three separate experiments. (C) BMDCs generated from C57BL/6 or il12rb1$^{-/-}$ mice (where il12rb1$^{-/-}$ indicates an absence of both IL12Rβ1 alleles as compared to il12rb1$^{+/+}$ which indicates that both IL12Rβ1 alleles are present) were assayed for their ability to migrate to CCL19 in a transwell assay after a 3 hr exposure to *M. tuberculosis* chemotaxis index (CI) represents the number moved in response to CCL19/number moved to media alone. Data points in (C) represent mean and standard deviation (SD) of triplicate values and are representative of three separate experiments; for the difference between CI induced in C57BL/6 relative to il12rb1$^{-/-}$ DCs, *p<0.05, **p<0.005 as determined by Student's t-test. (D-F) *M. tuberculosis*/CFSE was instilled via the trachea into C57BL/6, il12rb1$^{-/-}$ or il12rb2$^{-/-}$ mice. 18 hrs later the frequency (D,E) and total number (F) of $CD11c^+CFSE^+$ cells in the draining MLN were counted. The data points (E,F) represent the mean and SD of combined data from 4 mice per group and are representative of two separate experiments; for the difference between percentage and/or number of $CD11c^+$ $CFSE^+$ cells found in C57BL/6 mice relative to i/12b$^{-/-}$ or il12rb1$^{-/-}$ mice, *p<0.05, ***p<0.0005 as determined by Student's t-test.

The present invention relates generally to methods and compositions for both diagnostic and therapeutic applications. In one embodiment, the present invention contemplates a vaccine formulation comprising an antigen and a peptide isoform of the IL12 Receptor Beta 1 (IL12Rβ1) splice variant IL12Rβ1 ΔTM. In some embodiments this invention relates to a method of quantifying the ratio of IL12Rβ1 cDNA and a splice variant thereof in a sample. In other embodiments, this invention relates to a method of augmenting an immune response by administering, inhibiting and/or inducing a peptide isoform of the splice variant IL12Rβ1ΔTM.

I. Dendritic Cells

DCs are pivotal for initiating immunity to *M. tuberculosis* (Khader et al., 2006, Tian et al., 2005) and other diseases of the pulmonary tract (Lambrecht, 2008). The majority of individuals infected with *M. tuberculosis* control the infection through an acquired antigen-specific CD4$^+$ T-cell response (Mogues et al., 2001). The IL12 family of cytokines (i.e. IL12, IL23 and IL12(p40)$_2$) are essential to the generation of this response (Cooper, 2009), with IL12(p40)$_2$ being required for DCs to migrate following mycobacterial and other pathogenic stimuli (Khader et al., 2006, McCormick et al., 2008, Robinson et al., 2008). IL12 cytokine family members are also secreted by DCs following pathogen stimulation (Jang et al., 2008, Robinson et al., 2008) and are required for their ability to generate an efficient T cell response (Robinson et al., 2008, Zhang et al., 2003). After encountering *M. tuberculosis*, CD11c$^+$ DCs migrate from the lung to the draining mediastinal lymph node (MLN) where they present *M. tuberculosis* antigen(s) to T cells (Wolf et al., 2007). Activated T cells then localize to the infected lung where they express various effector mechanisms. As an illustration of the importance of proper CD11c$^+$ migration and function, CD11c$^+$ depletion prior to *M. tuberculosis* infection delays the CD4$^+$ T cell response and exacerbates the outcome of infection (Tian et al., 2005).

II. IL12Rβ1

IL12 family members mediate their biological activities through specific, high affinity dimeric receptors. These receptors all share IL12Rβ1, a 100 kDa glycosylated protein that spans the plasma membrane and serves as a low affinity receptor for the IL12p40-subunit of IL12 family members (Chua et al., 1994, Chua et al., 1995). Co-expression of IL12Rβ1 with IL12Rβ2 or IL23R results in high affinity binding of IL12 and IL23, respectively, and confers biological responsiveness to these cytokines (Parham et al., 2002, Presky et al., 1996, van Rietschoten et al., 2000). Polymorphisms in IL12β or IL12Rβ1 are associated with psoriasis (Capon et al., 2007), atopic dermatitis and other allergic phenotypes (Takahashi et al., 2005). Since IL12Rβ1 mediates the activity of cytokines such as IL-12p70, IL-23 and IL-12 (p40)$_2$ it has the potential to impact many aspects of the immune responses; including for example enhancing protective immunity to pathogens as well as regulating the damaging effects inflammatory responses associated with autoimmune pathologies (such as arthritis).

A large body of data demonstrates the essential function that the IL12Rβ1 gene serves in humans to positively regulate immunity to mycobacterial pathogens. For example, non-functional IL12Rβ1 alleles predispose an individual to mycobacterial susceptibility (Altare et al., 1998, de Jong et al., 1998, Filipe-Santos et al., 2006, Fortin et al., 2007). The association between IL12Rβ1 deficiency and mycobacterial susceptibility undoubtedly reflects the importance of the IL12Rβ1 gene to a wide variety of cell types. Thus, understanding how IL12Rβ1 expression and IL12Rβ1-dependent signaling is regulated has important implications for tuberculosis and may impact other diseases.

In some embodiments, following *M. tuberculosis* infection DCs express IL12Rβ1 and an alternatively spliced variant of IL12Rβ1 mRNA termed IL12Rβ1ΔTM mRNA. This splice variant can be detected at the mRNA level on $CD11c^+$ cells from the lungs of *M. tuberculosis* infected mice and as a protein in the membrane of DCs. In contrast to IL12Rβ1, IL12Rβ1ΔTM mRNA encodes an altered C-terminal sequence and is lacking a transmembrane-domain; nevertheless the IL12Rβ1ΔTM protein is still membrane associated. While the expression of IL12Rβ1 mRNA is increased during active pulmonary tuberculosis in humans (Taha et al., 1999), expression of human IL12Rβ1ΔTM mRNA during pulmonary tuberculosis has never been assessed.

III. Alternative Splicing

Alternative splicing is emerging as an important regulator of immunity (Lynch, 2004). It is estimated that >75% of human genes undergo alternative splicing, many of which are exclusively expressed by the immune system (Johnson et al., 2003). The list of proteins regulated by splicing include those involved in intracellular signaling cascades (i.e. Fyn, Syk), membrane adhesion (i.e. CD31, CD44 and CD54) and cell activation (i.e. CD45 and CD152)(Lynch, 2004). Alternatively spliced cytokine receptors can regulate inflammatory events by functioning as either agonists or antagonists of cytokine signaling (Levine, 2004). The list of alternatively splice cytokine receptors include members of the class I cytokine receptor superfamily (IL4R, IL5R, IL6R, IL7R, IL9R, EpoR, GCSFR, GMCSFR, gp130, and LIFR), class II cytokine receptor superfamily (IFNAR1 and IFNAR2), IL-1/TLR family (IL1RII, IL1RAcP), TGF-receptor family (TRI, activin receptor-like kinase 7), TNFR superfamily (TNFRSF6/Fas/CD95, TNFRSF9/4-1BB/CD137 and the IL17R (Levine, 2004). In some embodiments, IL12Rβ1ΔTM can now be added to this list of spliced and functioning cytokine receptors.

The mouse IL12Rβ1 and IL12Rβ1ΔTM cDNAs were originally cloned based on their nucleotide homology to human IL12Rβ1 (Chua et al., 1995). When transfected into COS cells, both cDNAs produced proteins that bind $[^{125}I]$-IL12 with similar low affinities, suggesting that IL12Rβ1 and IL12Rβ1ΔTM proteins were both expressed on the cell surface (Chua et al., 1995). However no function has been ascribed to IL12Rβ1ΔTM. In one embodiment, it is now demonstrated that while mouse IL12Rβ1ΔTM cannot substitute for IL12Rβ1, it can function in DCs to enhance IL12 $(p40)_2$ and IL12Rβ1-dependent migration and promote $CD4^+$ T cell activation in response to *M. tuberculosis* infection. In a preferred embodiment, expression of IL12Rβ1ΔTM by DCs therefore serves as a (previously unknown) positive-regulator of IL12Rβ1-dependent events. Selective reconstitution of $il12rb1^{-/-}$ DCs with IL12Rβ1 and/or IL12Rβ1ΔTM demonstrates that IL12Rβ1ΔTM can augment, but not substitute for, IL12101-dependent DC migration. In vivo relevance is demonstrated by experiments demonstrating 1) that lung $CD11c^+$ cells express IL12Rβ1ΔTM after *M. tuberculosis* infection and 2) that reconstitution of il12rb1 DCs with IL12Rβ1 and IL12Rβ1ΔTM accelerates in vivo $CD4^+$ T cell activation as compared to $il12rb1^{-/-}$ DCs reconstituted with IL12Rβ1 alone. That this may be relevant to the understanding of human DC biology is suggested by the observation that human peripheral blood mononuclear cell (PBMC)-derived DCs also respond to stimulation by splicing IL12Rβ1 mRNA. Surprisingly, the stimuli that elicit IL12Rβ1 mRNA splicing are broader in origin for humans than for mice.

Results demonstrate that the IL12Rβ1ΔTM protein is induced in cells exposed to the pathogen *M. tuberculosis* and that it is expressed in vivo in the lungs of mice infected with this pathogen. Results further indicate that the IL12Rβ1 ΔTM protein augments IL12 signaling by ligands of the IL12 receptor complex and increases the chemotactic activity of motile cells. Since IL12 is required for induction of cellular responses that limit mycobacterial disease and is also required to promote type-1 cellular responses, in one embodiment the IL12Rβ1ΔTM protein may be used to augment vaccine induced IL12 expression and increase type-1 immune responses to vaccination.

Results also demonstrate that $IL12(p40)_2$ enhances *M. tuberculosis*-dependent NFκB activation. $IL12(p40)_2$ is produced by migrating DCs (Robinson et al., 2008) and IL12B sufficient DCs are more efficient at migrating to the draining lymph node and stimulating T-cell responses than IL12B deficient DCs (Khader et al., 2006, Reinhardt et al., 2006, Robinson et al., 2008). That $IL12(p40)_2$ can activate NFκB-dependent events has also been observed in microglial cells (Dasgupta et al., 2008). Since it lacks any known intracellular signaling capacity, in one embodiment the IL12Rβ1ΔTM protein may enhance IL12Rβ1-signaling by increasing the affinity of $IL12(p40)_2$ for IL12Rβ1 or by forming some other structure that favors $IL12(p40)_2$-signaling. In particular, as IL12p40 binds only to dimer/oligomers of IL12Rβ1 protein (Chua et al., 1995), another embodiment it is possible that the IL12Rβ1ΔTM protein stabilizes oligomerization of the IL12Rβ1 protein.

In a preferred embodiment, these findings present a pathway whereby a deficiency in IL12Rβ1ΔTM results in an impaired ability to control *M. tuberculosis* infection. The expression of IL12Rβ1 mRNA and IL12Rβ1ΔTM mRNA in the $CD11c^-$ fraction of *M. tuberculosis*-infected lungs suggests that the proteins encoded by these sequences may play a role during the chronic stage of infection. Results clearly indicate that for mouse DCs, both *M. tuberculosis* and *M. avium* are capable of eliciting IL12Rβ1 mRNA splicing whereas *Y. pestis* stimulation is not. This may reflect the activation of distinct Toll-like receptor (TLR) cascades. IL12Rβ1ΔTM expression is likely not restricted to DCs and may augment functions other than migration.

IV. Experimental

The following are examples that further illustrate embodiments contemplated by the present invention. It is not intended that these examples provide any limitations on the present invention. In the experimental disclosure that follows, the following abbreviations apply: eq. or eqs. (equivalents); M (Molar); µM (micromolar); N (Normal); mol (moles); mmol (millimoles); µmol (micromoles); nmol (nanomoles); pmoles (picomoles); g (grams); mg (milligrams); µg (micrograms); ng (nanograms); vol (volume); w/v (weight to volume); v/v (volume to volume); L (liters); ml (milliliters); µl (microliters); cm (centimeters); mm (millimeters); µm (micrometers); nm (nanometers); C (degrees Centigrade); rpm (revolutions per minute); DNA (deoxyribonucleic acid); kdal (kilodaltons).

a) IL12Rβ1 is Required for *M. Tuberculosis*-Induced DC Migration and Function

CD11c$^+$ cells are essential for the control of *M. tuberculosis* infection (Tian et al., 2005) and IL12(p40)$_2$ is required for their migration in response to pathogenic stimuli (Khader et al., 2006, McCormick et al., 2008, Robinson et al., 2008). Since IL1213 is required for DC migration in response to *M. tuberculosis* (Khader et al., 2006), it was therefore necessary to determine whether the IL12Rβ1 gene—which encodes the receptor for IL12β (Oppmann et al., 2000, Presky et al., 1998, Wang et al., 1999)—is expressed by DC in response to *M. tuberculosis* and if it is required for subsequent DC migration and T cell priming.

Delivery of *M. tuberculosis* via the intratracheal route revealed that the frequency of CD11c$^+$ cells expressing IL12Rβ1 in the lungs increases three hours after delivery (FIG. 1A). Bone marrow-derived DCs (BMDCs) also respond to *M. tuberculosis* by increasing IL12Rβ1 expression on CD11c$^+$ cells (FIG. 1B). An immature population of il12rb1$^{-/-}$ BMDC was generated to determine if IL12Rβ1 was required for DC migration following mycobacterial stimulation, based on their ability to migrate towards the homeostatic chemokine CCL19 using a previously established method (Khader et al., 2006). DCs are morphologically and phenotypically similar to C57BL/6 DCs (data not shown); however in an in vitro transwell assay DCs had a significantly lower migratory response towards CCL19 after exposure to varying concentrations *M. tuberculosis* compared to C57BL/6 controls (FIG. 1C). To determine if this was also true in vivo, an emulsion of *M. tuberculosis* and carboxyfluorescein succinimidyl ester (CFSE) was administered to il12b$^{-/-}$, il12rbr$^{-/-}$, il12rb2$^{-/-}$ and C57BL/6 mice via the trachea and the number of CD11c$^+$ CFSE$^+$ cells in the draining MLN was determined 18 hours later. While non-manipulated mice of all genotypes had similar numbers of CD11c$^+$ cells in their lung and MLN (data not shown), a lower frequency (FIG. 1D, E) and fewer numbers (FIG. 1F) of CD11c$^+$ CFSE$^+$ cells in the MLN of il12b$^{-/-}$ and il12rb1$^{--/-}$ was consistently observed in mice after administration of *M. tuberculosis* and CFSE via the trachea. This was not true of il12rb2$^{-/-}$ mice, further supporting a role for IL12(p40)$_2$ and not IL12p70 in DC migration (Khader et al., 2006). These results demonstrate that IL12Rβ1 is required for *M. tuberculosis*-induced CD11c$^+$ cell migration from the lung to the draining MLN.

b) A Reduced Frequency of IL12Rβ1-Sufficient CD11c$^+$ Cells in the Lung Delays the Activation of *M. Tuberculosis*-Specific T Cells CD4$^+$ T cell responses to *M. tuberculosis* antigens are initiated in the MLN (Gallegos et al., 2008, Reiley et al., 2008, Winslow et al., 2008, Wolf et al., 2008). Therefore a delay in CD11c$^+$ cell migration should delay the activation of *M. tuberculosis*-specific CD4$^+$ T cells. To test this theory diphtheria toxin (DT) was used to specifically deplete il12rb1$^{+/+}$ CD11c$^+$ cells from bone marrow chimeras that contain diphtheria toxin receptor positive (DTR$^+$) C57BL/6 CD11c$^+$ cells and DTR negative il12rb1$^{-/-}$ CD11c$^+$ cells. *M. tuberculosis*-specific T cell activation to intratracheal administration of *M. tuberculosis* antigen was then measured. The chimeras were generated by reconstituting lethally irradiated C57BL/6 mice with 25% and 75% Itgax-DTR/eGFP bone marrow (DTR:il12rb1$^{-/-}$ mice) or, as a control, 25% C57BL/6 and 75% Itgax-DTR/eGFP bone marrow (DTR: WT mice). The Itgax-DTR/eGFP mice are transgenic for a simian DTR fused to an enhanced green fluorescent protein (eGFP) that is under control of the Itgax (or CD11c) promoter. Upon DT administration, CD11c$^+$ cells containing this transgene are transiently depleted in most tissues (Jung et al., 2002).

Figure 2:
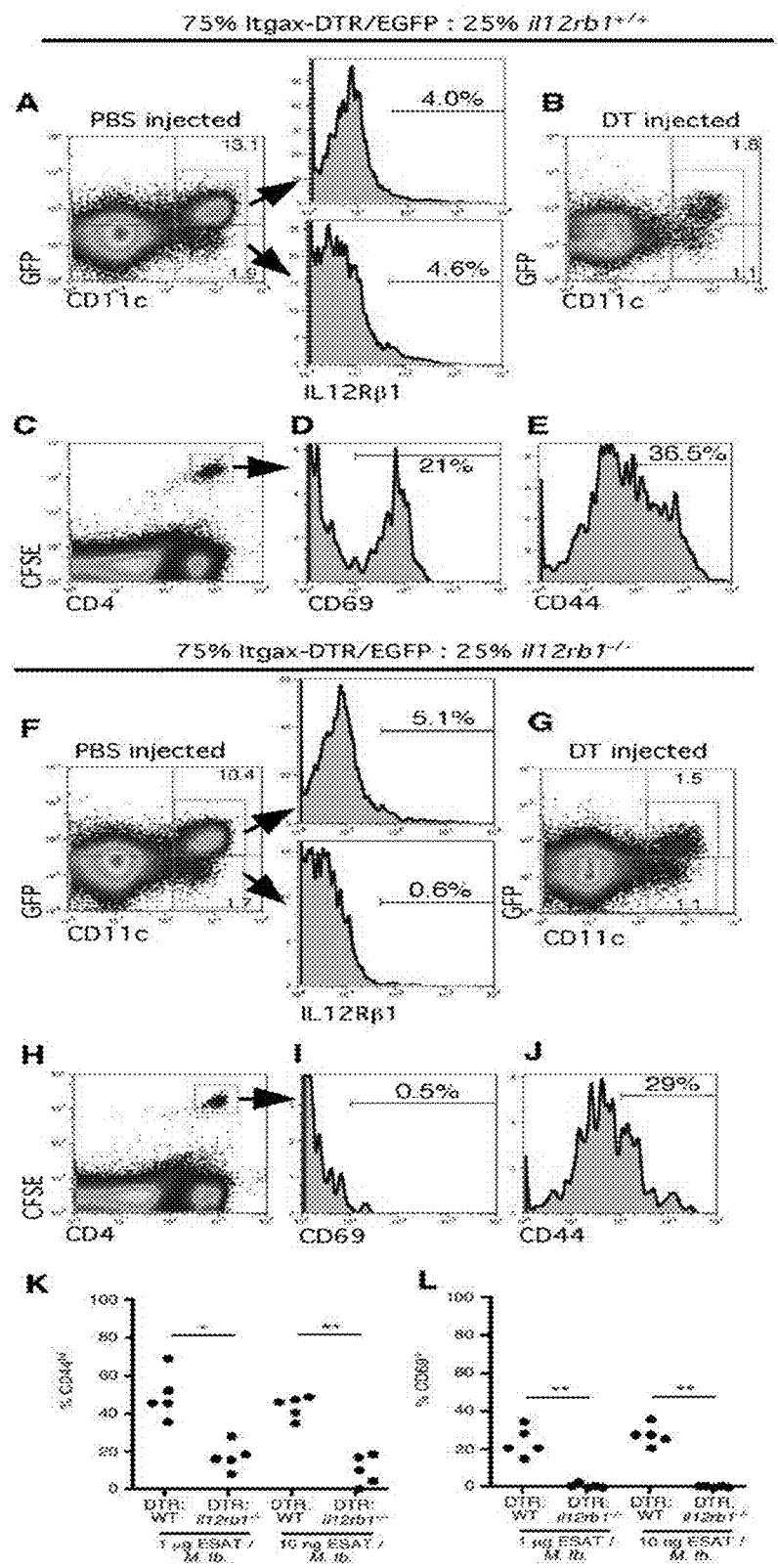
FIG. 2 demonstrates that the presence of il12rb1$^{-/-}$ DCs in the lung associates with impaired activation of *M. tuberculosis*-specific T cells in the draining MLN. Chimeras comprising 75% Itgax-DTR/EGFP:25% il12rb1$^{+/+}$ or 75% Itgax-DTR/EGFP:25% il12rbr$^{-/-}$ were injected with either PBS (A,F) or DT (B-E, G-J). 12 hrs later the frequency of $CD11c^+$ $GFP^+$ and $CD11c^+GFP^-$ cells remaining in the lungs after PBS injection (A,F) or DT injection (B,G) was determined. Gating based on $CD11c^+$ $GFP^+$ or $CD11c^+$ $GFP^-$ cells demonstrated the level of IL12Rβ1 surface expression (A,F). DT injected mice subsequently received $1.5 \times 10^6$ CFSE-labeled $ESAT_6$-specific $CD4^+$ T cells and 1 μg $ESAT6_{1-20}$/50 ng irradiated *M. tuberculosis* via the trachea. 12 hrs later the frequency of $CFSE^+CD4^+$ cells in the draining MLN (C, H) and expression levels of the activation markers CD69 (D, I) and CD44 (E, J) were determined by flow cytometry. The data points (K, L) represent the CD44 (K) and CD69 (L) data from 5 mice per group that received either 1 μg or 10 ng $ESAT_{1-20}$ peptide with irradiated *M. tuberculosis* and are representative of two separate experiments; for the difference in % $CD44^{hi}$ and % $CD69^+$ ESAT-specific $CD4^+$ cells between the indicated groups, *p<0.05, **p<0.005 as determined by Student's t-test.

In control DTR:WT mice injected with saline the majority of CD11c$^+$ cells are GFP$^+$, demonstrating reconstitution of the lung with DTR expressing cells (FIG. 2A). Both GFP$^+$ and the subset of GFP$^-$ CD11c$^+$ cells are il12rb1$^{+/+}$ and express basal levels of IL12Rβ1 protein on their surface (FIG. 2A). Upon injection of DT the frequency of GFP$^+$ CD11c$^+$ cells drops approximately 12 fold (FIG. 2B), resulting in an increased ratio of GFP$^-$ to GFP$^+$ CD11c$^+$ cells. Treating the DTR:il12rb1$^{-/-}$ mice with DT resulted in a similar drop in GFP$^+$ CD11c$^+$ cells (FIGS. 2F-G) and therefore a greatly reduced frequency of il12rb1$^{+/+}$CD11c$^+$ relative to il12rb1$^{-/-}$ CD11c$^+$ cells in the lungs of these mice.

To compare the relative T cell activating ability of lungs harboring a high frequency of il12rb1$^{+/+}$ CD11c$^+$ cells to those with a low frequency, the response of antigen-specific cells in the MLN was measured. To this end 1.5×10$^6$ CFSE-labeled ESAT-specific CD4$^+$ T cells (Reiley et al., 2008) were intravenously transferred into DT injected DTR:WT or DTR: il12rb1$^{-/-}$ mice immediately prior to instillation via the trachea of ESAT6$_{1-20}$ peptide and 1 µg of irradiated *M. tuberculosis*. Eighteen hours later the frequency of ESAT-specific T cells (FIG. 2C and FIG. 2H) expressing markers of activation CD69 (FIG. 2D and FIG. 2I) and CD44 (FIG. 2E and FIG. 2J) in the draining MLN was determined. The frequency of ESAT6-specific T cells that expressed a high level of CD69 (FIG. 2K) and CD44 (FIG. 2L) in response to two different doses of antigen within the 18 hours of the experiment was significantly lower in the mice with a reduced frequency of il12rb1$^{+/+}$ CD11c$^+$ cells. Thus, an increase in the ratio of il12rb1$^{-/-}$ to il12rb1$^{+/+}$ DCs in the lungs is associated with impaired activation of antigen-specific T cells in the draining MLN. These data demonstrate that IL12Rβ1 expression in CD11c$^+$ cells within the lung is required for *M. tuberculosis*-induced DC migration and induction of T cell activation in vivo.

c) IL12(p40)$_2$ Initiates Nuclear Accumulation of NF-κB in DCs

Figure 3:
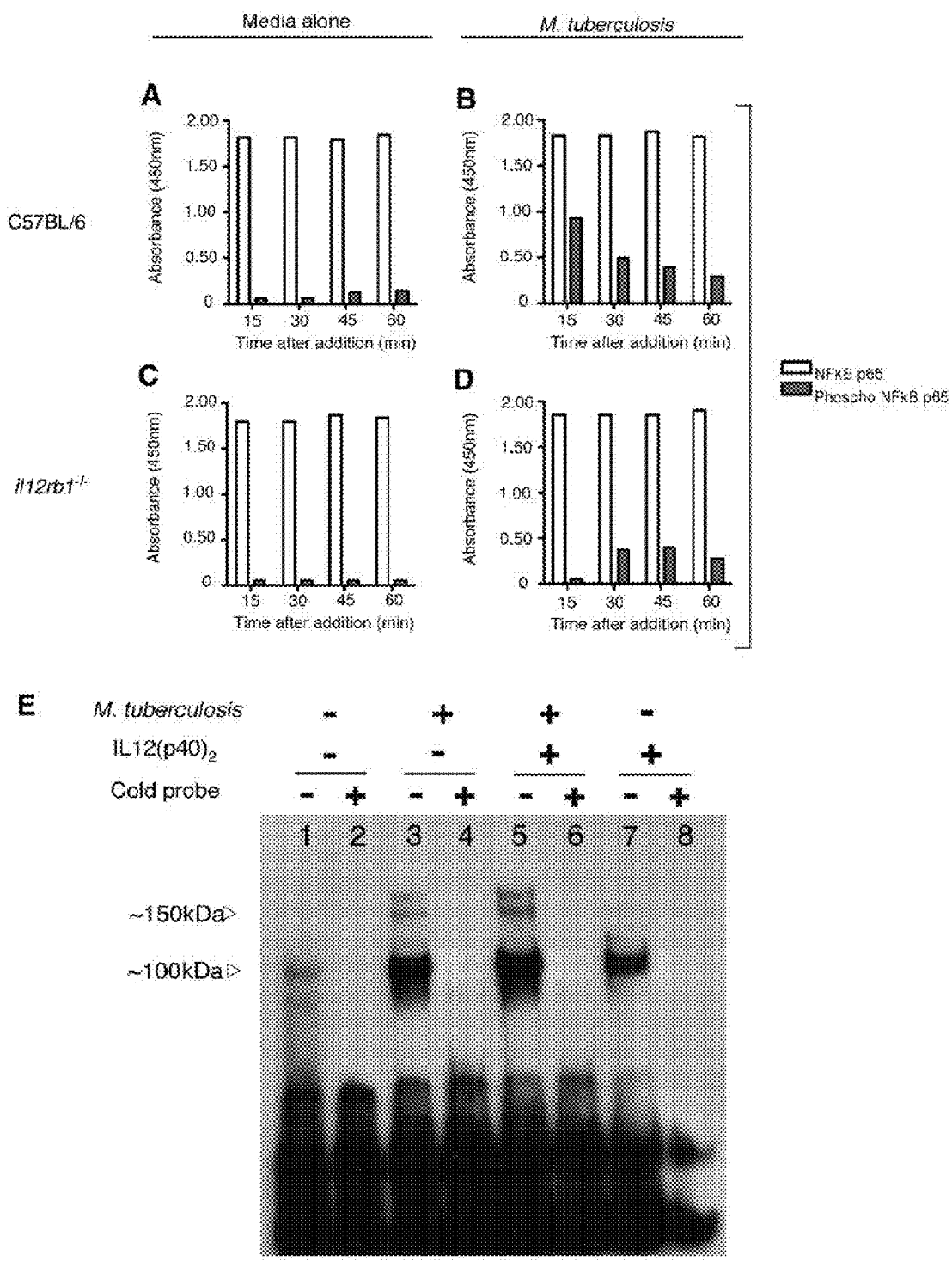
FIG. 3 demonstrates that NFκB signaling is impaired in il12rb1$^{-/-}$ DCs and can be promoted by IL12(p40)$_2$. BMDCs generated from C57BL/6 and il12rb1$^{-/-}$ mice were exposed to *M. tuberculosis* (B, D) or media alone (A, C) for the indicated times. Cells were then harvested under non-denaturing conditions and levels of total NFκB p65 (open bars) and phospho-NFκB p65 (closed bars) were determined by ELISA. Shown are the absorbance values ($A_{450}$) from one experiment that is representative of three. (E) BMDCs were generated from il12b$^{-/-}$ mice and exposed to media alone, *M. tuberculosis*, IL12(p40)$_2$, or both *M. tuberculosis* and IL12 (p40)$_2$. 1 hr later nuclear extracts of the treated cells were isolated and electromobility shift analysis (EMSA) of NFκB consensus sequence-binding proteins was performed. Shown is a blot of NFκB consensus sequence-binding proteins from DCs stimulated with media alone (lanes 1, 2), *M. tuberculosis* (lanes 3, 4), both *M. tuberculosis* and IL12(p40)$_2$ (lanes 5, 6) or IL12(p40)$_2$ alone (lanes 7, 8). The absence (−) or presence (+) of a cold NFκB consensus probe was used to determine the specificity of each band.

There is a need to better understand the mechanism by which IL12Rβ1-dependent signaling modulates DC chemotaxis following exposure to *M. tuberculosis*. Lower levels of CCR7 (the receptor for CCL19) do not account for this result, as surface expression of CCR7 is similar between activated wild type and il12rb1$^{-/-}$ BMDCs (data not shown). To determine if any intracellular signaling pathways that influence DC migration were altered in il12rb1$^{-/-}$ DCs, phosphorylation levels of NF-κB, SAPK/JNK, p38α MAP Kinase and STAT3 were measured in these cells following stimulation with *M. tuberculosis*. Results demonstrated that stimulation of C57BL/6 DCs increases phospho-NF-κB levels above those of unstimulated controls (FIG. 3A, B). However, levels of phospho-NF-κB were consistently observed to be lower in il12rb1$^{-/-}$ DCs compared to wild type DCs at several time points despite equivalent levels of total NF-κB (FIG. 3C, D).

No differences in phospho-SAPK/JNK, p38α MAP Kinase and STAT3 were observed between wild type and il12rbr$^{-/-}$ DCs (data not shown). These data suggest that NFκB dependent processes are compromised in il12rb1$^{-/-}$ DCs.

Since NFκB phosphorylation was defective in il12rb1$^{-/-}$ DCs, it was reasoned that NFκB binding should be enhanced when DCs are stimulated via IL12Rβ1. To test this hypothesis BMDC were exposed to *M. tuberculosis* and/or IL12(p40)$_2$ for 1 hour and the amount of NFκB consensus sequence-binding proteins in nuclear extracts of the treated cells was compared via electromobility shift assay (EMSA). il12b$^{-/-}$ BMDCs were used for this experiment to eliminate potential background NFκB activation from endogenous IL12(p40)$_2$. FIG. 3E demonstrates that the addition of *M. tuberculosis* to DC cultures increases the nuclear accumulation of NFκB over that seen in untreated BMDC (compare lanes 1 and 3). IL12(p40)$_2$ was also sufficient to increase the nuclear accumulation of NFκB over that seen in untreated BMDC (compare lanes 1 and 7). The addition of both *M. tuberculosis* and IL12(p40)$_2$ synergistically augmented NFκB activation above that of each stimulus alone (compare lanes 3 and 7 to lane 5). Thus, the data demonstrate that IL12(p40)$_2$ is able to stimulate NFκB nuclear migration in DCs. Consequently, the failure of il12rb1$^{-/-}$ DCs to migrate (FIG. 1-2) associates with impaired NFκB-dependent gene activation.

d) BMDCs Express IL12Rβ1 mRNA and an IL12Rβ1 mRNA Alternative Splice Variant After Exposure to *M. Tuberculosis*

Figure 4:
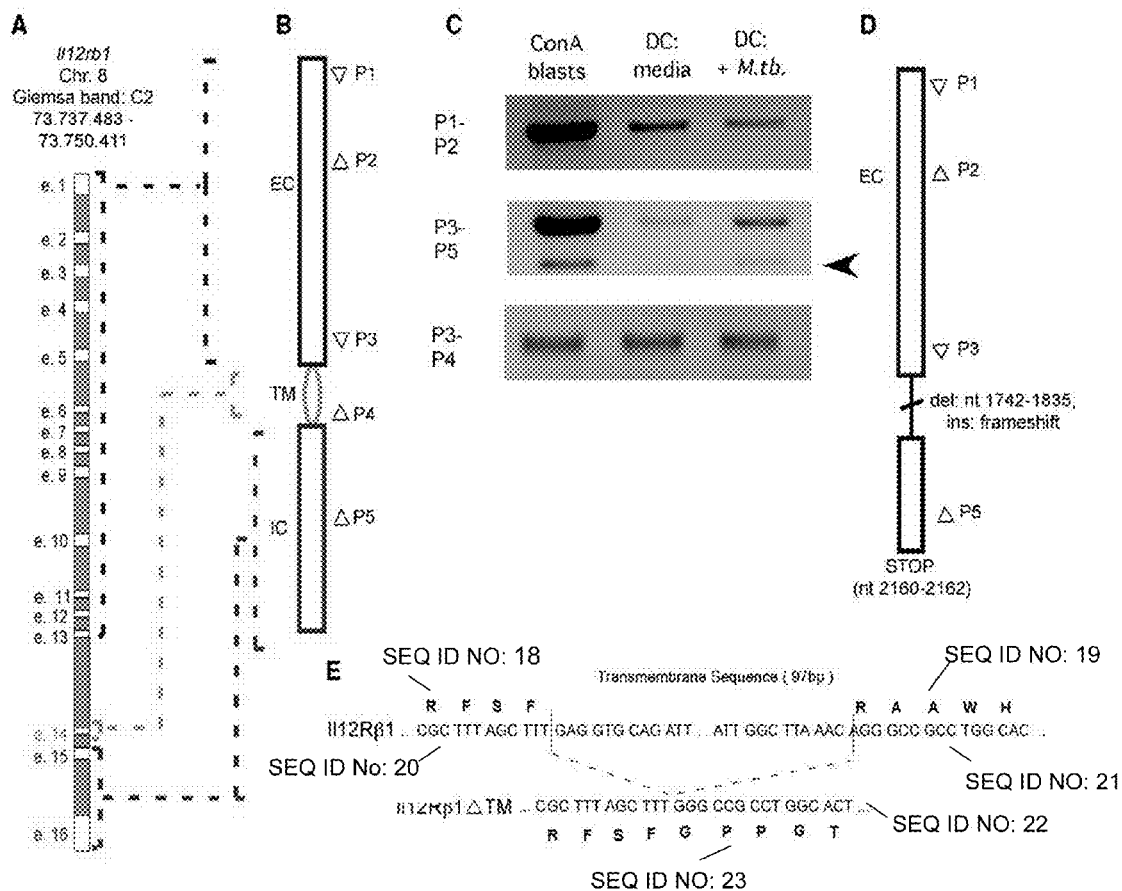
FIG. 4 demonstrates that DCs express an IL12Rβ1 mRNA alternative splice variant following exposure to *M. tuberculosis*. (A) The genomic position and organization of the murine IL12Rβ1 locus. Exons 1-16 are denoted e.1-e.16. Upon transcription and intron-removal (B) e.1-13 becomes the extracellular-encoding (EC) portion of the IL12Rβ1 transcript, e.14 the transmembrane-encoding (TM) portion, and e15-16 the intracellular-encoding (IC) portion. Shown to the right of the transcript are the relative positions of primers 1-5 (P1-P5; ∇ indicates a forward primer and Δ indicates a reverse primer) used for (C) amplification of IL12Rβ1 cDNA from the indicated cell populations. (D-E) Sequencing of the smaller amplicon of P3-P5 (indicated by arrow) reveals an IL12Rβ1 mRNA alternative splice variant that contains both a 97 bp deletion and (E) a frameshift insertion that eventually produces a premature stop codon.

While DC's are not a commonly acknowledged target for the inflammatory cytokine IL-12, reports have indicated that the subunits of the receptor for IL-12 are expressed in these cells. The expression of IL12Rβ1ΔTM mRNA by DCs has not been universally accepted due to an inability to reproducibly detect this transcript (Grohmann et al., 1998); including the inability to amplify the IL12Rβ1 transcript with primers spanning the distal portion of exon 16. However, given the influence of IL12Rβ1 on DC migration (FIG. 1-2) IL12Rβ1 mRNA expression in these cells was re-examined. Results indicate that careful use of primer sets allows for detection of an IL12Rβ1 gene product in these cells. The murine IL12Rβ1 gene is located on autosomal chromosome 8C2 at position 73.737.483-73.750.411 and comprises 16 exons (FIG. 4A; NCBI GeneID 16161). Upon transcription and intron-removal, exons 1-13 are translated into the extracellular portion of the IL12Rβ1 protein, while exon 14 and exons 15-16 are translated into the transmembrane (TM) and intracellular portions, respectively (FIG. 4B). To determine the transcription activity of this gene in DCs, cDNA from BMDC cultures were amplified with a variety of primers spanning different lengths of IL12Rβ1 cDNA (FIG. 4B; forward and reverse primers are indicated by ∇- and Δ-arrows, respectively). Amplification with primers (P) recognizing the extracellular-encoding region (P1-P2) resulted in an amplicon (FIG. 4C); cDNA from concanavalin-A activated splenocytes is used as a positive control (IL12Rβ1$^{+/+}$). Confirming the results of Grohmann et al., amplification of DC cDNA with primers that recognize the intracellular encoding region (P3-P6) did not result in a visible amplicon from DC cDNA. However, amplification of a more 3' region with primers P3-P5 did result in a PCR product in both unstimulated and stimulated DCs. Surprisingly, under these amplification conditions a second smaller band was also observable, but only in DCs that had been stimulated with *M. tuberculosis* (see arrow, FIG. 4C). This second band does not appear upon amplification with primers that span the TM-encoding region (P3-P4). Sequencing both the larger and smaller band amplified by primers P3-P5 revealed that the larger product represents IL12Rβ1 mRNA and that the smaller product is identical except for a 97-bp deletion (FIG. 4D). This deletion has two effects: (1) Deletion of the TM sequence encoded by exon 14 and (2) a translational frame shift that results in an early stop codon. This translational frame shift also results in the loss of the Box1/2 signaling domains that are found in the IL12Rβ1 protein (van de Vosse et al., 2003). Both the nucleotide and deduced amino acid sequence of this smaller band (FIG. 4E) match that of a previously reported alternative splice variant of the mouse IL12Rβ1 transcript (Chua et al., 1995). Thus, DCs respond to *M. tuberculosis* by expressing two species of IL12Rβ1 mRNA: a transmembrane-containing transcript referred to as IL12Rβ1 mRNA and an alternatively spliced variant of IL12Rβ1 mRNA referred to as IL12Rβ1 ΔTM mRNA. It is interesting that IL12Rβ1ΔTM remains membrane-associated despite the absence of a transmembrane-domain. It is believed that IL12Rβ1ΔTM also functions to enhance IL12Rβ1-dependent processes in T and NK cells.

e) Kinetics of BMDC IL12Rβ1ΔTM mRNA Expression Following Exposure to *M. tuberculosis*

Figure 5:
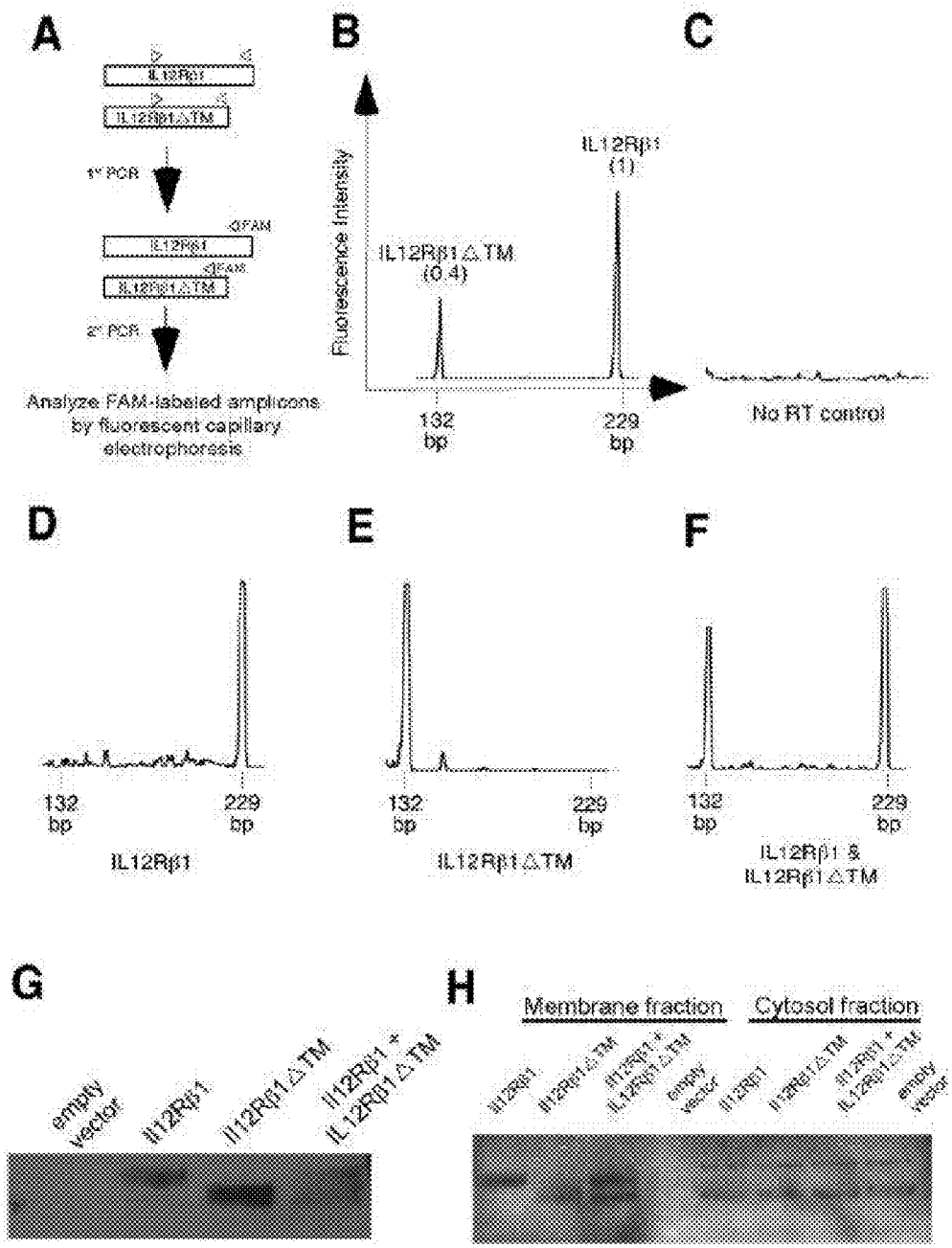
FIG. 5 illustrates the steps involved in IL12Rβ1 Spectratype analysis. (A) cDNA is first amplified with primers that flank the transmembrane-encoding region in order to amplify both IL12Rβ1 and IL12Rβ1ΔTM; the resultant amplicons are then fluorescently (FAM)-labeled via a run-off PCR reaction with a single FAM-conjugated primer. Given the published sequence of IL12Rβ1 and IL12Rβ1ΔTM (Chua et al., 1995), the FAM-labeled amplicons of these transcripts have a predicted size of 229 bp and 132 bp, respectively. (B) Analyzing the samples by fluorescent capillary electrophoresis allows the FAM-labeled products to be separated by size and their relative abundance to one another quantified. To demonstrate this, two peaks of the anticipated sizes are observed using cDNA of concanavalin-A activated splenocytes; neither are observed in no-reverse-transcriptase controls, ruling out genomic DNA amplification (C). Using the area under the larger, transmembrane containing fluorescent peak as a unit reference, the relative abundance of IL12Rβ1ΔTM can be determined. The numbers adjacent to peaks of individual IL12Rβ1 spectra indicate the relative ratio of that peak's area (the smaller peak representing IL12Rβ1ΔTM) to the area of the larger peak that represents IL12Rβ1. In concanavalin A-activated splenocytes, the ratio of IL12Rβ1ΔTM to IL12Rβ1 was observed to be 0.4:1 (B). To further test the fidelity of this assay to distinguish between IL12Rβ1 and IL12Rβ1ΔTM, NIH/3T3 cells were transfected with mammalian expression vectors containing each respective cDNA. IL12Rβ1 Spectratype analysis of single- (D, E) and double-transfectants (F) revealed that the 229 bp and 132 bp peaks observed via this assay do in fact represent IL12Rβ1 and IL12Rβ1 ΔTM, respectively. Importantly, western blot analysis with polyclonal anti-IL12Rβ1 confirmed that IL12Rβ1ΔTM could be translated into a protein product as first demonstrated by Chua et al. (Chua et al., 1995) (G). Subcellular fractionation of cell membrane and cell cytosol confirmed IL12Rβ1ΔTM to be membrane associated as first predicted by Chua et al. (Chua et al., 1995) (H).
Figure 6:
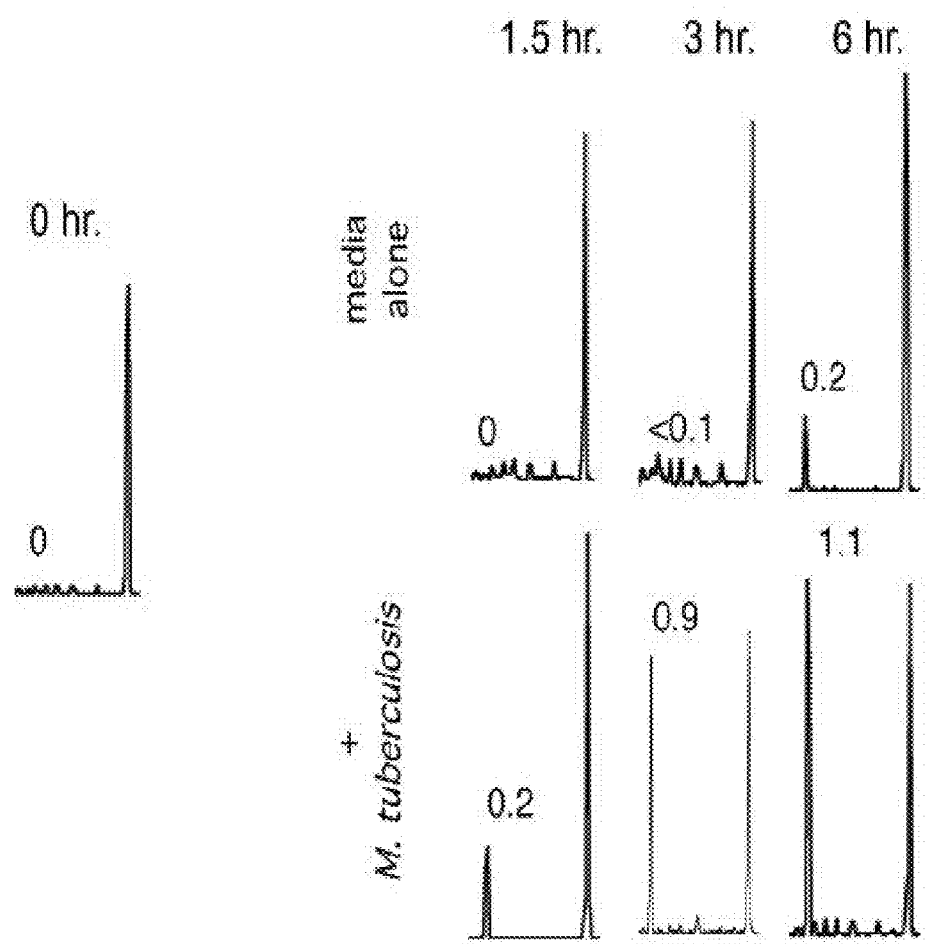
FIG. 6 depicts the L12Rβ1 Spectratype analysis of *M. tuberculosis*-activated DCs. (A) C57BL/6 bone marrow-derived DCs were stimulated over a period of 6 hrs with media alone or *M. tuberculosis*. Shown are representative IL12Rβ1 spectratype data from these DCs before culture (0 hr) and after 1.5, 3 or 6 hrs of culture. The numbers adjacent to peaks of individual IL12Rβ1 spectra indicate the relative ratio of that peak's area (the smaller peak representing IL12Rβ1ΔTM) to the area of the larger peak that represents IL12Rβ1. Spectra are representative of four mice per condition; this experiment was performed twice. (B) Denaturing western analysis of the same cells to confirm changing protein levels of Th1212.131 and IL12Rβ1ΔTM; recombinant IL12Rβ1 and NIH/3T3 cells transfected with the indicated plasmid constructs served as positive controls; blots were probed with polyclonal anti-IL12Rβ1.
Figure 6:
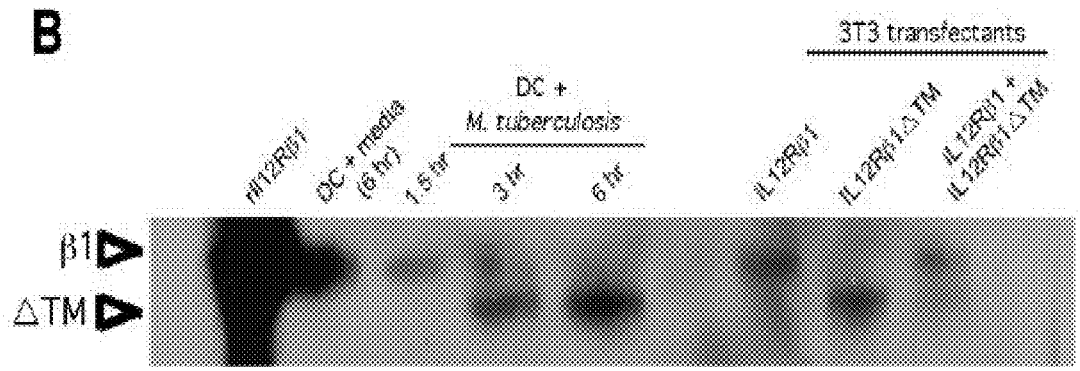

Attempts to quantify IL12Rβ1ΔTM mRNA expression induced in BMDCs by *M. tuberculosis* proved difficult due to an inability to design a Taqman real time PCR probe that recognized IL12Rβ1ΔTM cDNA and not IL12Rβ1 cDNA. To better quantify the kinetics of IL12Rβ1ΔTM mRNA expression relative to IL12Rβ1 mRNA in *M. tuberculosis*-stimulated DCs, a PCR-based assay was developed—hereafter referred to as "IL12Rβ1 Spectratype analysis". IL12Rβ1 Spectratype analysis is akin to TCR-CDR3 Spectratype analysis (Pannetier et al., 1993) and is described in FIG. 5. When IL12Rβ1 Spectratype analysis was applied to BMDCs, a dose-dependent increase in the ratio of IL12Rβ1ΔTM mRNA to IL12Rβ1 mRNA was observed after a 3-hour exposure to *M. tuberculosis* (FIG. 6A). In contrast IL12Rβ1 mRNA remains the dominant transcript in unstimulated DCs for up to 6-hours (FIG. 6A). Western blot analysis demonstrated that IL12Rβ1 is the dominant protein product in unstimulated cells while IL12Rβ1 ΔTM protein increases in abundance following *M. tuberculosis* stimulation (FIG. 6B). That IL12Rβ1ΔTM protein could locate in the membrane was indicated by Western blot analysis of cellular fractions (FIG. 5H). Thus, analysis of mRNA and Western blot analysis confirm that DCs increase the expression of IL12Rβ1ΔTM mRNA and production of IL12Rβ1ΔTM protein following exposure to *M. tuberculosis*.

Figure 7:
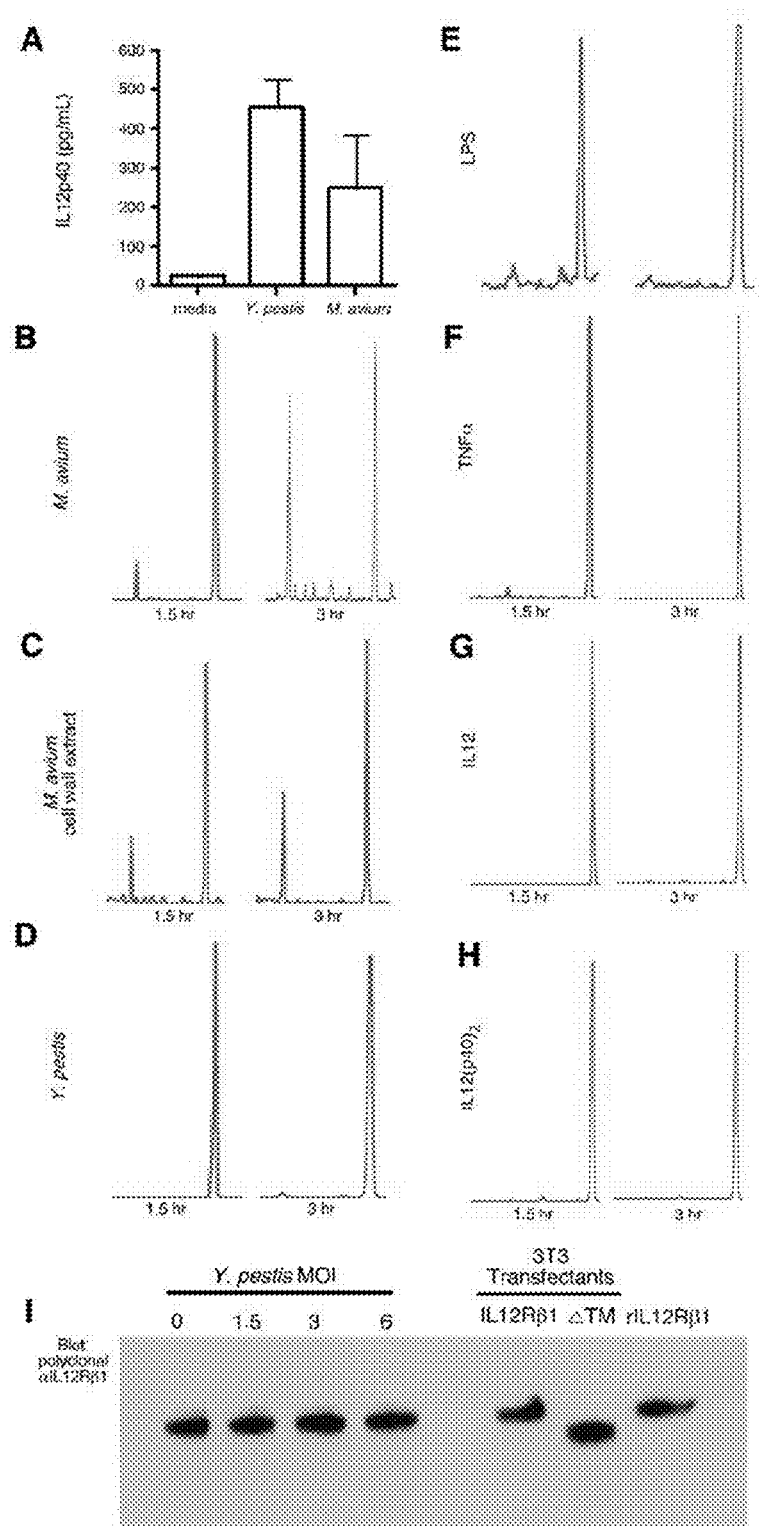
FIG. 7 depicts IL12Rβ1ΔTM expression by BMDCs following exposure to *M. avium*, *M. avium* cell wall extract, *Y. pestis*, LPS, TNFα, IL12 or IL12(p40)$_2$. DCs prepared from C57BL/6 bone marrow were exposed in vitro to either media alone, *Y. pestis* (5 MOI), *M. avium* (5 MOI), *M. avium* cell wall extract, *E. coli* LPS or to cytokines TNFα, IL12 and IL12(p40)$_2$ for 3 hrs. At the end of 1.5 and 3 hr periods DC RNA was collected for IL12Rβ1 Spectratype analysis. (A) Measurement of IL12p40 in the DC supernatant by ELISA served as a positive control that both *Y. pestis* and *M. avium* were capable of stimulating DCs. (B-H) Representative IL12Rβ1 spectra from 1.5 hr and 3 hr following exposure to (B) *M. avium*, (C) *M. avium* cell wall extract, (D) *Y. pestis*, (E) LPS, (F) TNFα, (G) IL12 or (H) IL12(p40)$_2$. (I) Western Blot demonstrating that IL12Rβ1 ΔTM peptide production is not observed after stimulation of DCs with varying MOI of *Y. pestis*.

To assess the specificity of IL12Rβ1 mRNA splicing in response to *M. tuberculosis*, DCs were stimulated with a variety of other microbial and cytokine stimuli. Specifically, DCs were stimulated with *M. avium* and *Y. pestis* (at an identical MOI) as well as with *M. avium* cell wall extract, *Escherichia coli* lipopolysaccharide (LPS), TNFα, IL12 and IL12(p40)$_2$. Production of IL12Rβ1ΔTM mRNA was subsequently assessed by IL12Rβ1 Spectratype analysis. Both *M. avium* and *Y. pestis* were capable of activating DCs as measured by IL12p40 production (FIG. 7A). As shown in FIG. 7B, over a 3-hour incubation *M. avium* was capable of eliciting IL12Rβ1 ΔTM production with kinetics that were similar to that elicited by *M. tuberculosis*. This was also observed with *M. avium* cell wall extract (FIG. 7C). Stimulation with *Y. pestis* and purified LPS (FIG. 7D-E) failed to generate IL12Rβ1ΔTM over the same 3-hour period. Negative results were also obtained with TNFα, IL12 and IL12(p40)$_2$-stimulated DCs (FIG. 7F-H). Thus, DCs increase the expression of IL12Rβ1ΔTM not only in response to *M. tuberculosis* but also to the related organism *M. avium*; stimulation with gram negative *Y. pestis*, purified LPS and cytokines TNFα, IL12 and IL12(p40)$_2$ fails to elicit this same response.

f) Human DCs Respond to Stimuli by Splicing IL12Rβ1

Figure 8:
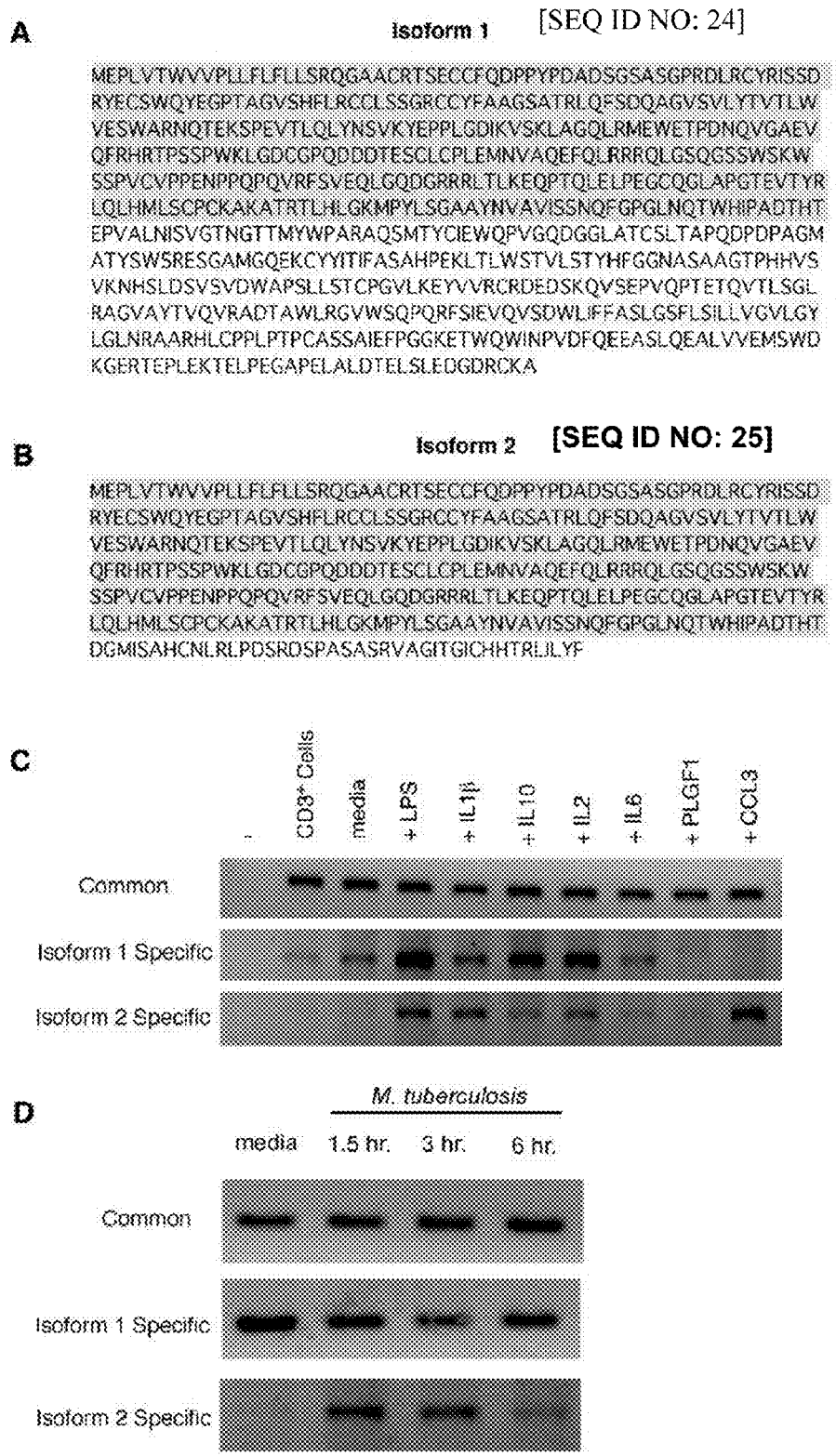
FIG. 8 depicts the expression of two IL12Rβ31 isoforms by human DCs following exposure to *M. tuberculosis* and other specific stimuli. (A-B) Two isoforms of the human IL12Rβ31 transcript are reported in publicly available databases: full length IL12Rβ31 (isoform 1; Swiss-Prot ID P42701-1) and a shorter isoform that is the product of alternative splicing (isoform 2; Swiss-Prot P42701-3). The amino acid sequences of (A) isoform 1 (SEQ ID NO: 24) and (B) isoform 2 (SEQ ID NO: 25) are reproduced. (C-D) Monocyte-derived DCs were generated by incubating magnetically purified CD 14$^+$ monocytes from apheresis samples for seven days with GMCSF and IL4. (C) DCs were then incubated for three days with either media alone, IL1β, IL10, IL2, IL6, PLGF1, CCL3 or for 24 hours with LPS. (D) Alternatively, DCs were stimulated with *M. tuberculosis* over a 6 hr period. Subsequently generated cDNA from both (C-D) was then amplified with primer pairs that either amplified both isoforms 1 and 2 (Common), only isoform 1 (isoform 1 specific) or only isoform 2 (isoform 2 specific), cDNA from CD3$^+$ PBMCs was used as a positive control for IL12Rβ1 expression.
Figure 9:
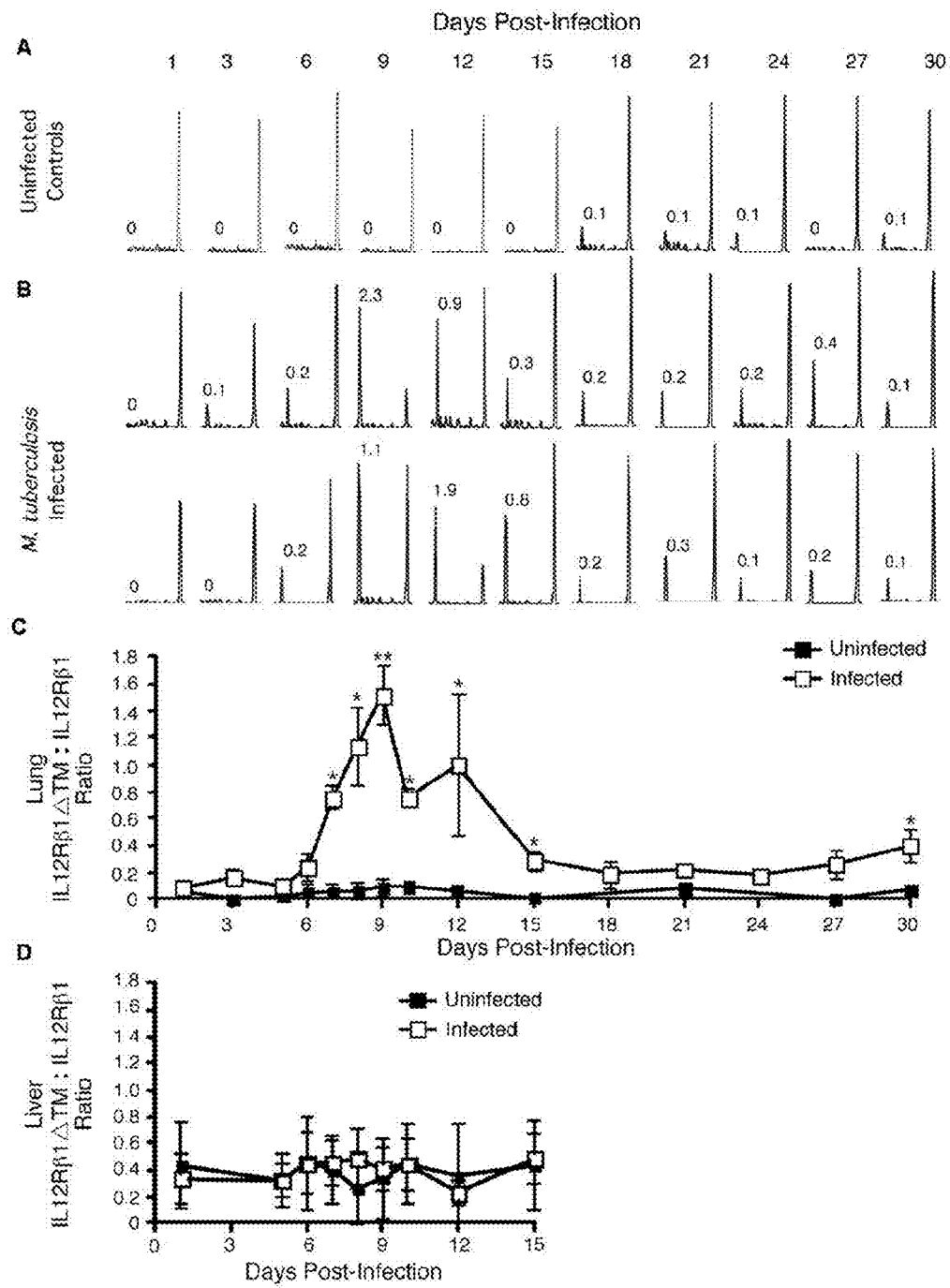
FIG. 9 depicts IL12Rβ1ΔTM expression in *M. tuberculosis*-infected lungs. C57BL/6 mice were aerogenically infected with 100 CFU *M. tuberculosis*. At the indicated times post-infection the lungs of both (A) uninfected and (B) infected mice were harvested for IL12Rβ1 Spectratype analysis. Shown are representative spectra from (A) one individual uninfected mouse at each indicated time point or (B) two individual *M. tuberculosis*-infected mice from each time point. The numbers adjacent to peaks of an individual IL12Rβ1 spectra indicate the relative ratio of that peak's area (the smaller peak representing IL12Rβ1ΔTM) to the area of the larger peak that represents IL12Rβ1. (C) The ratio of IL12Rβ1ΔTM to IL12Rβ1 expressed in the lung of uninfected and *M. tuberculosis*-infected animals. (D) The ratio of IL12Rβ1ΔTM to IL12Rβ1 expressed in the liver of uninfected and *M. tuberculosis*-infected animals. Data points in (C-D) represent the mean and SD of the IL12Rβ1ΔTM to IL12Rβ1 ratios expressed in 4-8 individual mice per time point; for the difference between infected lungs relative to uninfected lungs, *p<0.05, **p<0.005 as determined by Student's t-test.

Following their activation, human DCs increase surface expression of IL12Rβ1 (Nagayama et al., 2000). Two isoforms of the human IL12Rβ1 mRNA transcript are reported in publicly available databases: full length IL12Rβ1 (isoform 1; Swiss-Prot ID P42701-1) and a shorter isoform that is the product of alternative splicing (isoform 2; Swiss-Prot P42701-3). These sequences are available at http://www.uniprot.org/uniprot/P42701 and are reproduced in FIG. 8A-B. To determine if human DCs splice the IL12Rβ1 transcript following stimulation in a manner that is analogous to mouse DCs, monocyte-derived DCs were exposed to a variety of stimuli, some of which are known inducers of DC IL12Rβ1 expression (Nagayama et al., 2000). cDNAs generated from the stimulated DCs were assessed for the relative levels of transcripts for IL12Rβ1 isoforms 1 and 2 using specific primers; cDNA from $CD3^+$ PBMCs was used as a positive control. All samples (including DCs exposed to media alone) expressed IL12Rβ1 when assayed with primers that recognized both isoforms 1 and 2 (FIG. 8C, top panel). However, amplification with primers specific to either isoform 1 (FIG. 8C, middle panel) or isoform 2 (FIG. 8C, bottom panel) revealed that expression of these two transcripts was differentially regulated depending on the stimulus. Specifically, the production of isoform 2 was strongly associated with exposure to LPS, IL1β, IL2 and CCL3. Stimulation of human DCs with *M. tuberculosis* also elicited expression of IL12Rβ1 isoform 2 over a 6-hour time course (FIG. 8D). These experiments demonstrate that human DCs, like mouse DCs, respond to specific stimuli by splicing the IL12Rβ1 transcript.

g) IL12RA1 mRNA and IL12Rβ1ΔTM mRNA are Expressed by $CD11c^+$ Cells in the *M. tuberculosis*-Infected Lung IL12Rβ1ΔTM mRNA expression in response to *M. tuberculosis* infection in vivo was also examined by comparing the relative abundance of IL12Rβ1ΔTM mRNA to IL12Rβ1 mRNA over a time course in the lungs of mice aerogenically infected with *M. tuberculosis*. IL12Rβ1ΔTM abundance was analyzed in aerosol *M. tuberculosis* infected mice using a modified TCR CDR3 spectratyping assay with the ability to quantitate the relative ratios of two or more transcript sizes. In uninfected controls, the expression of IL12Rβ1ΔTM mRNA was minimal over the entire 30-day period, with IL12Rβ1 mRNA being the dominant transcript observed (FIG. 9A). In *M. tuberculosis*-infected animals, however, a shift in the ratio of IL12Rβ1ΔTM mRNA to IL12Rβ1 mRNA in the lung is observed at 9 days post-infection (FIG. 9B), with IL12Rβ1ΔTM mRNA reaching 2.4-fold higher abundance than IL12Rβ1 mRNA in some cases. After days 9-12, the ratio of IL12Rβ1ΔTM mRNA to IL12Rβ1 mRNA in the lung diminished but still remained higher than that of uninfected controls up to day 30. This result was observed in several independent experiments (FIG. 9C). In the liver (an organ distal to the initial site of infection) elevated baseline levels of IL12Rβ1ΔTM mRNA expression compared to the lung were observed (FIG. 9D); however these levels remained unchanged through the early course of *M. tuberculosis* infection (FIG. 9D). In summary, IL12Rβ1ΔTM mRNA is expressed subsequent to *M. tuberculosis* infection in vivo—the relative ratio to IL12Rβ1 mRNA being dependent upon time post-infection.

Figure 10:
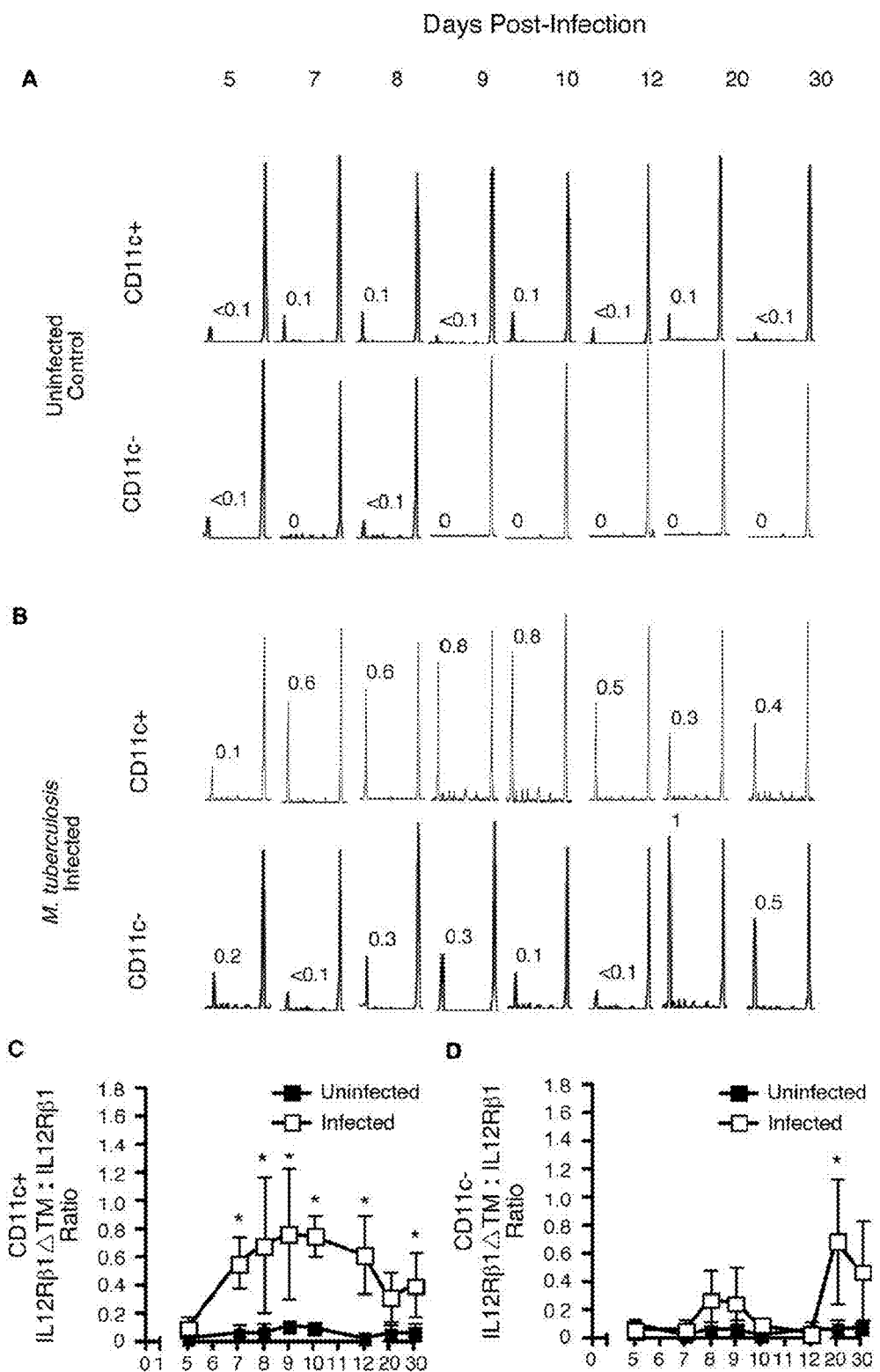
FIG. 10 depicts IL12Rβ1ΔTM expression in CD11c$^+$ and CD11c$^-$ populations following *M. tuberculosis*-infection. C57BL/6 mice were aerogenically infected with 100 CFU of *M. tuberculosis*. At the indicated times after infection, lung CD11c$^+$ and CD11c$^-$ populations were magnetically separated from both (A) uninfected and (B) infected mice. Subsequently generated cDNA was used for IL12Rβ1 Spectratype analysis. Representative spectra expressed by CD11c$^+$ and CD11c$^-$ cells from (A) an individual uninfected mouse at each time point or (B) an individual *M. tuberculosis*-infected mouse at each time point are shown. The numbers adjacent to peaks of an individual IL12Rβ1 spectrum indicate the relative ratio of that peak's area (the smaller peak representing IL12Rβ1ΔTM) to the area of the larger peak that represents IL12Rβ1. Spectra are representative of four mice per time point. (C) The ratio of IL12Rβ1ΔTM to IL12Rβ1 expressed by lung CD11c$^+$ cells from uninfected and *M. tuberculosis*-infected animals. (D) The ratio of IL12Rβ1ΔTM to IL12Rβ1 expressed by lung CD11c$^-$ cells from uninfected and *M. tuberculosis*-infected animals. Data points in (C-D) represent the mean and SD of the IL12Rβ1ΔTM to IL12Rβ1 ratios expressed in 4 individual mice per time point; for the difference between the indicated populations from infected lungs relative to uninfected lungs, *p<0.05 as determined by Student's t-test.

The expression of IL12Rβ1ΔTM by DCs in vitro (FIG. 6) and by the *M. tuberculosis*-infected lung in vivo (FIG. 9) prompted experiments to determine whether $CD11c^+$ cells from *M. tuberculosis*-infected lungs are the source of this transcript. $CD11c^+$ cells from the lungs of *M. tuberculosis*-infected mice were isolated by magnetic beads at various time points after infection and expression of IL12Rβ1ΔTM mRNA was determined as described in FIG. 9. $CD11c^+$ cells from *M. tuberculosis*-infected mice consistently expressed a higher ratio of IL12Rβ1ΔTM mRNA to IL12Rβ1 mRNA compared to those isolated from uninfected controls, the highest being observed at days 7-12 post-infection (compare top panels of FIG. 10A-B). Notably, the $CD11c^-$ cells from *M. tuberculosis*-infected mice also expressed a higher ratio of IL12Rβ1ΔTM mRNA to IL12Rβ1 mRNA compared to uninfected controls, the highest being observed at days 20 and 30 post-infection (compare lower panels of FIG. 10A-B). This result was observed in several independent experiments (FIG. 10C-D). These data demonstrate that following low dose aerogenic *M. tuberculosis* infection, lung $CD11c^+$ cells exhibit increased expression of IL12Rβ1ΔTM mRNA and that $CD11c^-$ cells can also express this transcript as infection progresses.

Figure 11:
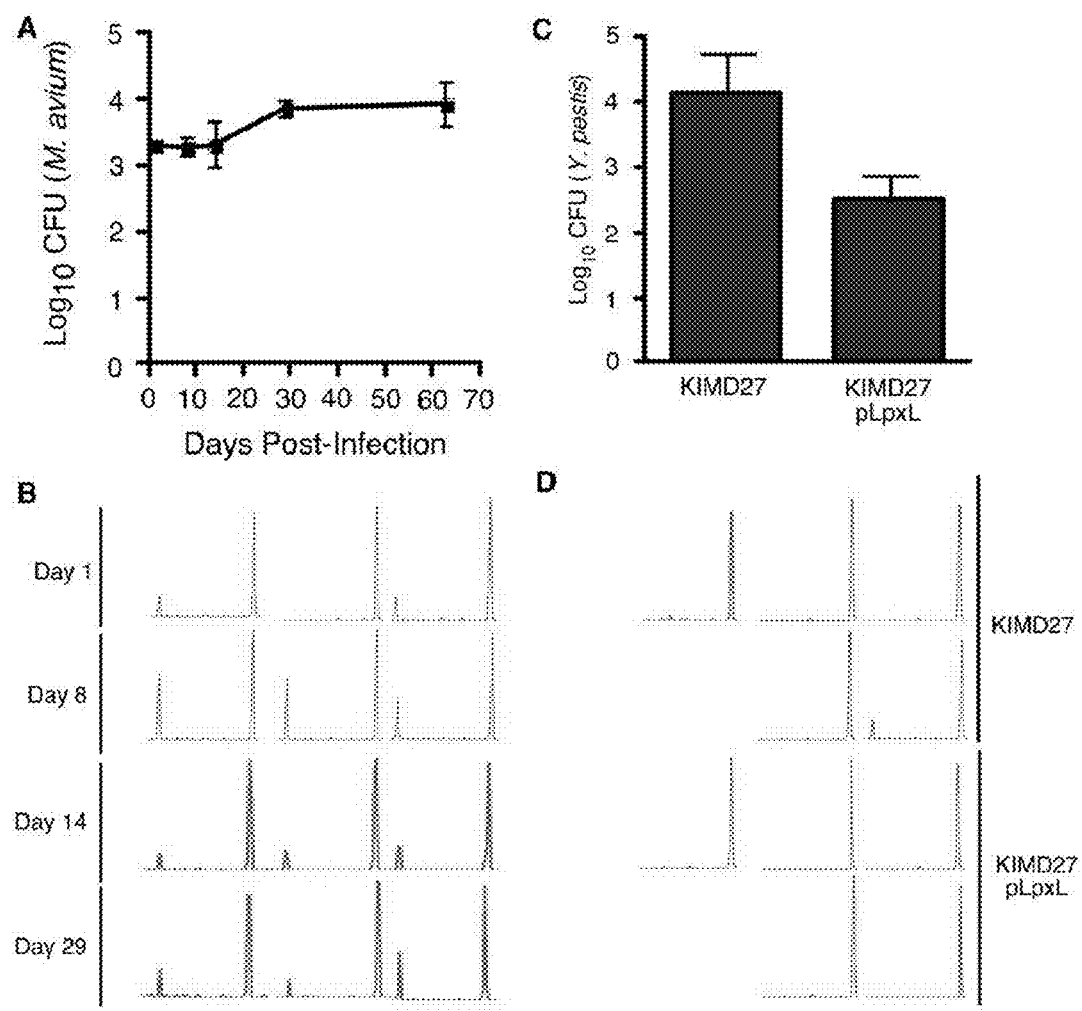
FIG. 11 depicts IL12Rβ1ΔTM expression in the lung following infection with *M. avium* or *Y. pestis*. C57BL/6 mice were aerogenically infected with 1×10$^3$ CFU of *M. avium* strain 2447. Shown in (A) are the *M. avium* CFU per lung at various times post-infection. (B) On days 1, 8, 14 and 29 post-infection total lung RNA was harvested for IL12Rβ1 Spectratype analysis. Shown are representative spectra from three individual *M. avium*-infected mice at each time point, with the smaller peak representing IL12Rβ1ΔTM and the larger peak representing IL12Rβ1. (C-D) C57BL/6 were intranasally infected with 1×10$^5$ CFU of *Y. pestis* strain KIMD27 or 1×10$^6$ CFU of *Y. pestis* strain KIMD27 pLpxL. Four days post-infection the lungs were harvested to both (C) determine the total CFU per lung and (D) assess total lung expression of IL12Rβ1ΔTM. Shown are the spectra from five individual *Y. pestis* KIMD27 or KIMD27 pLpxL infected mice at this time. Data points in (A, C) represent the mean number and SD of bacterial CFU present in the lungs of 4-5 individual mice per time point.

Similar to *M. tuberculosis*, *M. avium* and *Y. pestis* are lung-tropic intracellular pathogens. Since exposure to *M. avium*, but not *Y. pestis*, increased DC expression of IL12Rβ1ΔTM mRNA, it was next determined whether IL12Rβ1ΔTM mRNA was also expressed in the *M. avium* or *Y. pestis* infected lung. Mice were aerogenically infected with *M. avium* (FIG. 11A) or intranasally with *Y. pestis* KIMD27 (FIG. 11C) and a time course of IL12Rβ1ΔTM mRNA abundance relative to IL12Rβ1 mRNA was performed. As with *M. tuberculosis*, a shift in the ratio of IL12Rβ1ΔTM mRNA to IL12Rβ1 mRNA was observed in the lung at 9 days post-infection (FIG. 11B). Despite similar numbers of colony forming units (CFU) at day 4 post-infection, only one out of five *Y. pestis* infected animals showed expression of IL12Rβ1ΔTM mRNA (FIG. 11D, top panels). Negative results were also obtained upon infection with the more immunostimulatory strain *Y. pestis* KIMD27/pLpxL (FIG. 11D, bottom panels). Thus, in addition to *M. tuberculosis* (FIG. 11) expression of IL12Rβ1ΔTM mRNA in the lungs is also elicited by *M. avium*—but not *Y. pestis*.

h) IL12Rβ1ΔTM Enhances IL12Rβ1-Dependent Migration

DCs exhibit $IL12(p40)_2$ and IL12Rβ1-dependent migration in response to *M. tuberculosis* after only a 3 hour exposure to this organism (FIG. 1C and Khader et al., 2006, Robinson et al., 2008). Given that IL12Rβ1ΔTM mRNA is transcribed and translated within this timeframe (FIG. 6), and considered along with the ability of the IL12Rβ1ΔTM protein to bind the related protein IL12, the contribution of IL12Rβ1ΔTM to *M. tuberculosis*-induced, $IL12(p40)_2$-dependent DC migration was examined.

To address this issue an $IL12(p40)_2$-dependent NIH/3T3 migration assay (developed by Russell et al.) that models $IL12(p40)_2$-dependent DC migration using the commercially available NIH/3T3 mouse embryonic fibroblast cell line was used. Specifically, Russell et al. observed that NIH/3T3 cells transfected with IL12Rβ1 migrate towards $IL12(p40)_2$ while those that lack IL12Rβ1 do not. NIH/3T3 cells were split into four groups, and were transfected with either IL12Rβ1 alone, IL12Rβ1ΔTM alone, both IL12Rβ1 and IL12Rβ1ΔTM, or an empty vector control. All groups were cotransfected with eGFP to positively identify transfectants. Twenty-four hours later all groups were placed in the upper well of a Boyden chamber; the bottom well contained either $IL12(p40)_2$ or media alone. Enumerating the $GFP^+$ cells that migrated across the transwell allows IL12Rβ1ΔTM influenced transfectant migration toward $IL12(p40)_2$ to be determined. Results demonstrate that NIH/3T3 migration using this assay was both $IL12(p40)_2$ and IL12Rβ1-dependent (FIG. 13a).

Figure 13:
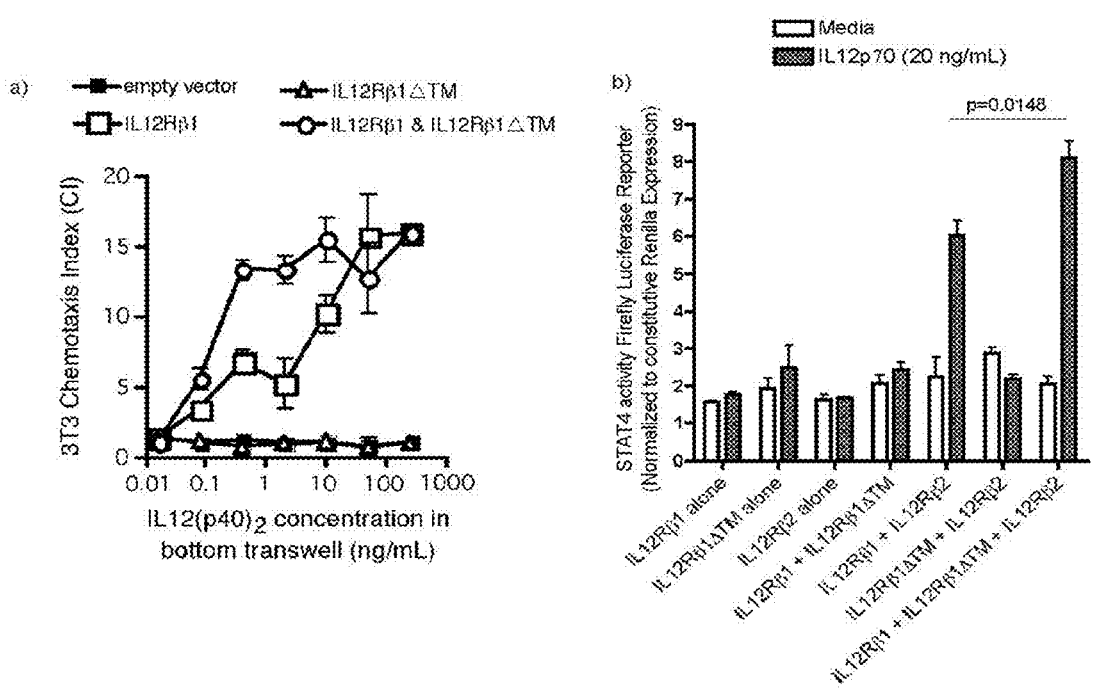
FIG. 13 depicts the role of IL12Rβ1ΔTM on IL12(p40)$_2$-dependent NIH/3T3 cell migration and STAT4 phosphorylation. (A) NIH/3T3 cells transfected with IL12Rβ1 alone, IL12Rβ1ΔTM alone, both IL12Rβ1ΔTM and IL12Rβ1 or empty vector were placed in the upper well of a Boyden chamber, while the bottom well contained either IL12(p40)$_2$ or media alone. (B) NIH/3T3 cells were transiently transfected with plasmids that constitutively express IL12Rβ1, IL12Rβ2 and STAT4. Following the addition of IL12, STAT4 phosphorylation is measured using a STAT4-reporter plasmid that contains firefly-luciferase under control of the GAS-promoter.

When IL12Rβ1ΔTM is substituted for IL12Rβ1, NIH/3T3 migration returns to media-alone levels. However co-transfection of IL12Rβ1ΔTM alongside IL12Rβ1 resulted in an approximate 50% increase in transfectant migration. These results are statistically significant and have been observed across several experiments (FIG. 13). Thus, while IL12Rβ1ΔTM cannot substitute for IL12Rβ1 it can augment IL12Rβ1-dependent NIH/3T3 cell migration.

Figure 12:
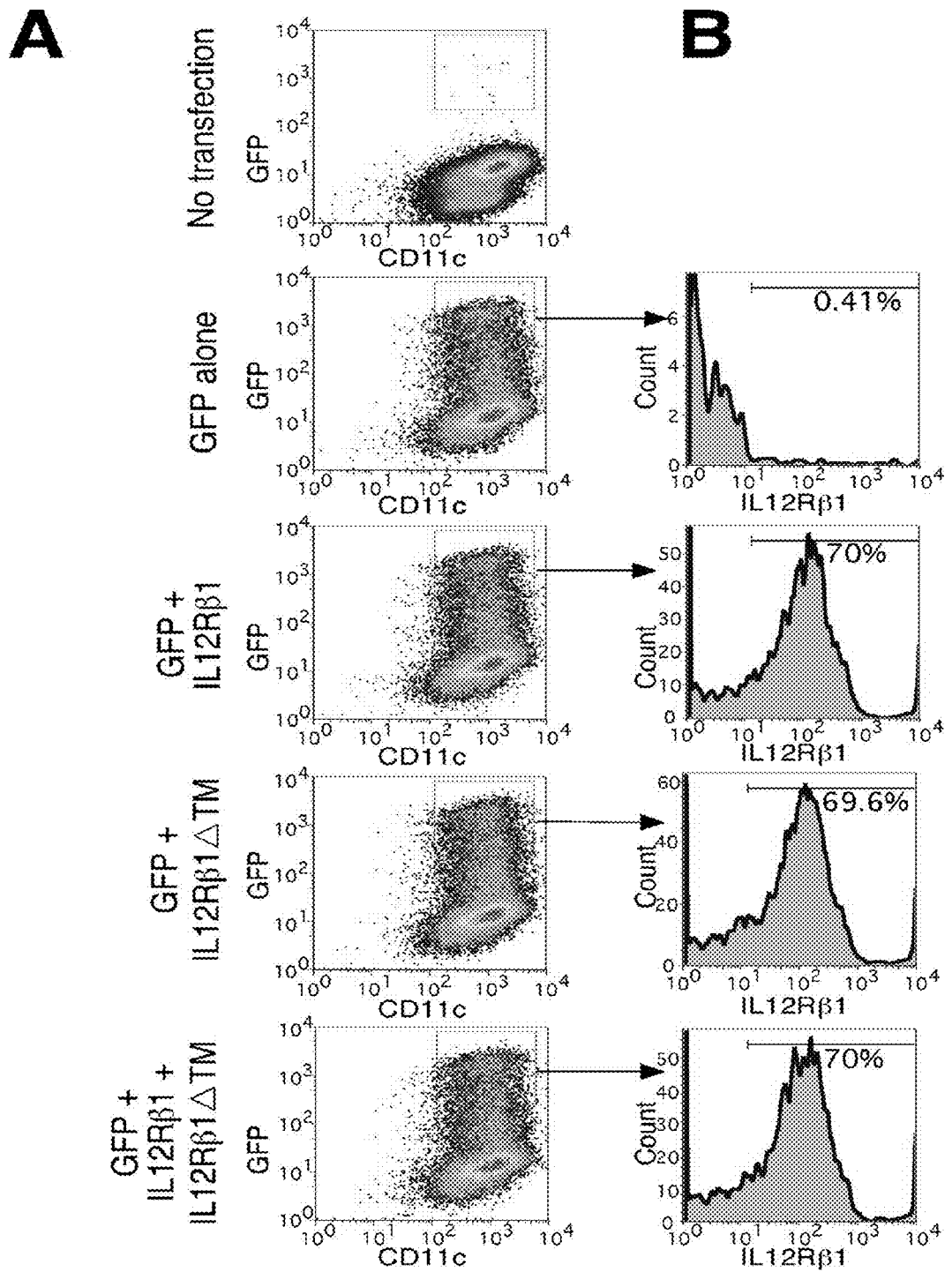
FIG. 12 demonstrates that IL12Rβ1ΔTM enhances IL12Rβ1-dependent migration. (A-D) il12rb1$^{-/-}$ CD11c$^+$ BMDCs were transfected with mRNAs encoding either GFP, GFP and IL12Rβ1, GFP and IL12Rβ1ΔTM or GFP and IL12Rβ1 and IL12Rβ1ΔTM. 24 hrs later (A) cells were analyzed by flow cytometry for GFP expression among CD11c$^+$ cells and (B) expression of transfected IL12Rβ1 was examined by gating on GFP$^+$CD11c$^+$ cells. (C) The migratory ability of DCs transfected with the indicated mRNAs was assessed as performed in FIG. 1C. Data points represent the mean and SD of the combined data from three separate experiments. For the difference between CI induced in the indicated groups, *p<0.05 as determined by Student's t-test. (D) Flow cytometric analysis of those cells that had migrated and transfected with GFP and IL12Rβ1 and IL12Rβ1ΔTM demonstrates that the migratory DCs from this group were mostly GFP$^+$. (E) The ability of il12rb1$^{-/-}$ DCs transfected with indicated mRNAs to activate *M. tuberculosis*-specific T cells in vivo was compared; sham-transfected C57BL/6 DCs were used as a positive control. Following transfection the indicated DCs populations were cultured with *M. tuberculosis* and ESAT$_{1-20}$ peptide; and then instilled via the trachea into C57BL/6 mice containing transferred CFSE-labeled ESAT-specific CD4$^+$ cells. Shown are histograms of CD44 and CD69 expression on CFSE$^+$CD4$^+$12 hrs later in the draining MLN. Each histogram is representative of four mice per condition. (F,G) The combined (F) CD44 and (G) CD69 data gated on CFSE$^+$ CD4$^+$ in the draining MLN are shown; these data are representative of two independent experiments.
Figure 12:
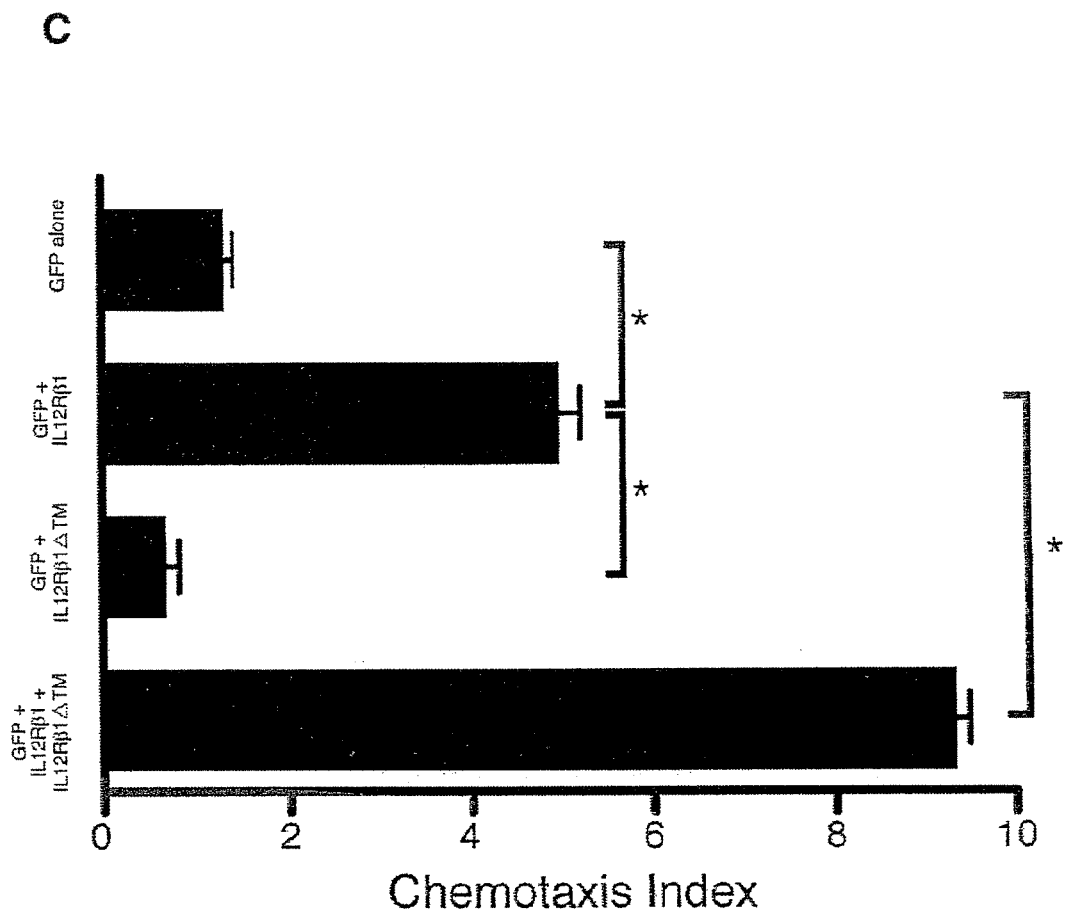
Figure 12D:
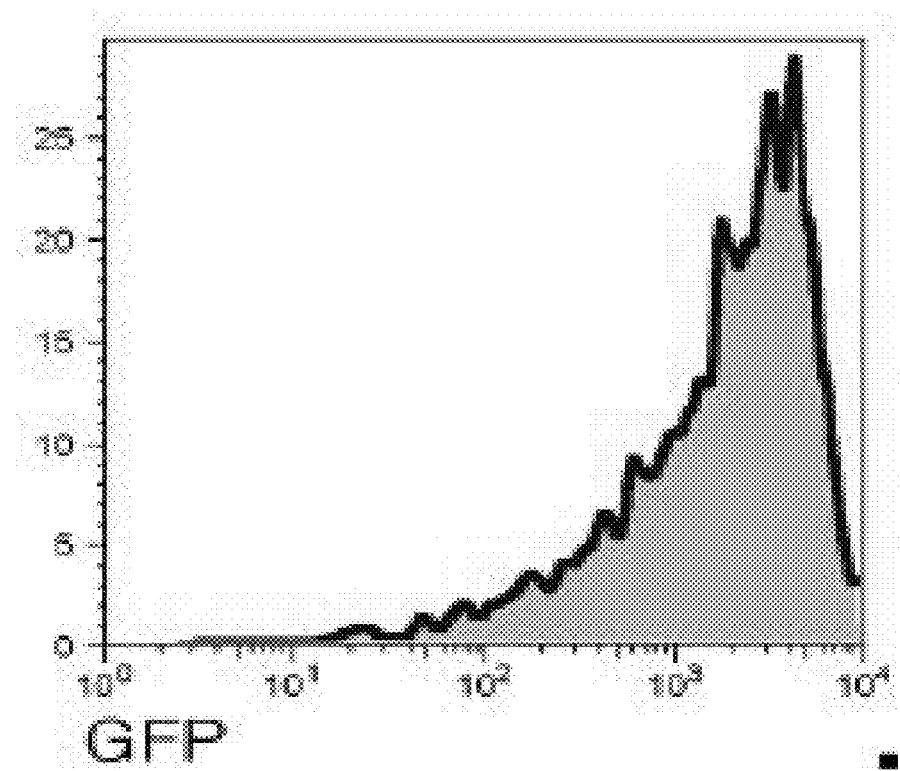

Related experiments were performed by selectively restoring mRNAs that encode IL12Rβ1, IL12Rβ1ΔTM, or both IL12Rβ1 and IL12Rβ1ΔTM to il12rb1$^{-/-}$ DCs which contain a genomic insertion of the neomycin resistance gene (neo insertion) that disrupts exons 1-3 of the IL12Rβ1 locus (Wu et al., 1997) and thus lacks both these proteins (FIG. 4). mRNA encoding GFP co-transfected with the specific mRNAs via electroporation demonstrated that an antibody specific for the common extracellular portion of IL12Rβ1 and IL12Rβ1ΔTM only labeled GFP$^+$ CD11c$^+$ cells if mRNAs for either IL12Rβ1 or IL12Rβ1ΔTM were delivered to the il12rb1$^{-/-}$ DCs (FIG. 12A and FIG. 12B). Following stimulation with *M. tuberculosis*, il12rb1$^{-/-}$ DCs transfected with GFP and IL12Rβ1 were capable of migrating toward CCL19 whereas those transfected with GFP alone were not (FIG. 12C). DCs transfected with GFP and IL12Rβ1ΔTM had migratory levels equivalent to those transfected with GFP alone. However, co-transfection with GFP, IL12Rβ1 and IL12Rβ1ΔTM resulted in a greater chemotaxis index than when DCs were transfected with GFP and IL12Rβ1. The majority of migrated cells were GFP positive suggesting that migration required transfection of the migrating cell and was not an indirect effect (FIG. 12D). These data demonstrate that IL12Rβ1ΔTM can enhance IL12Rβ1-dependent DC migration.

Figure 12E:
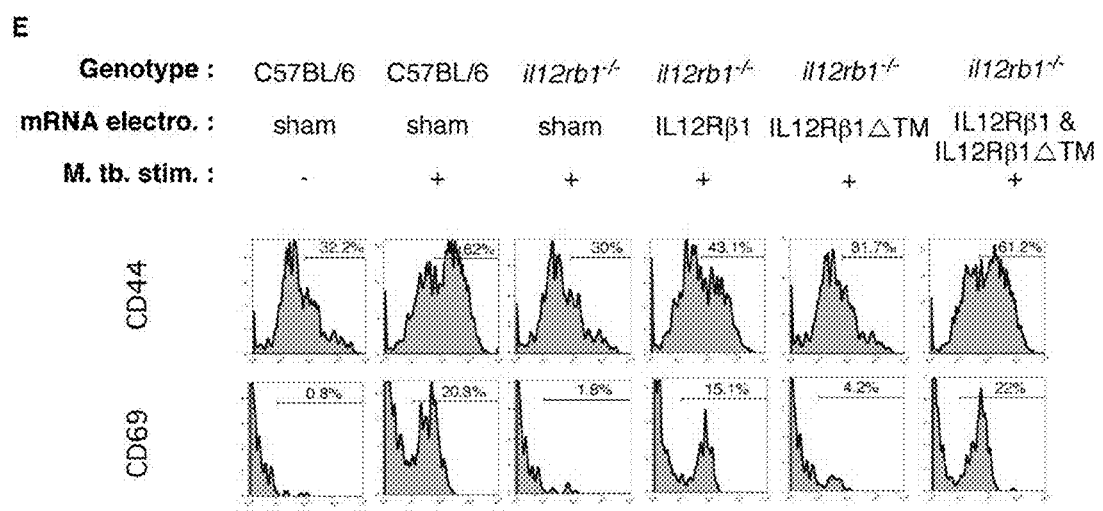
Figure 12F:
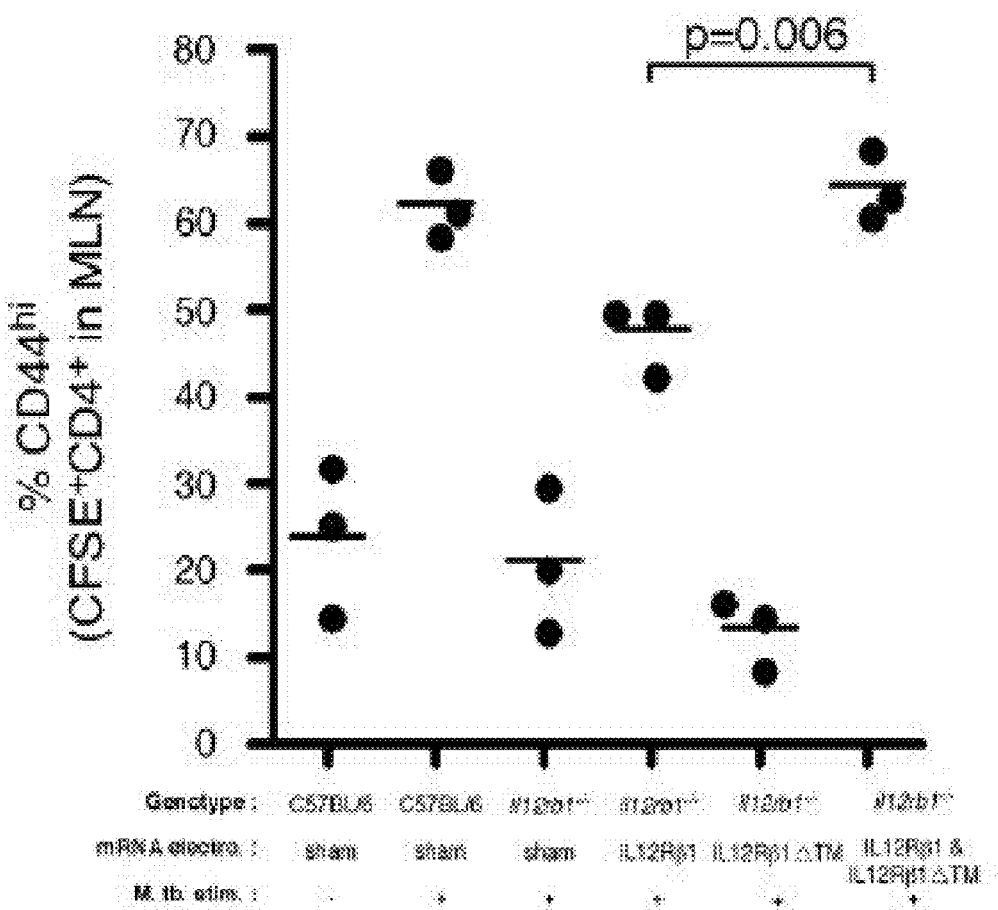
Figure 12G:
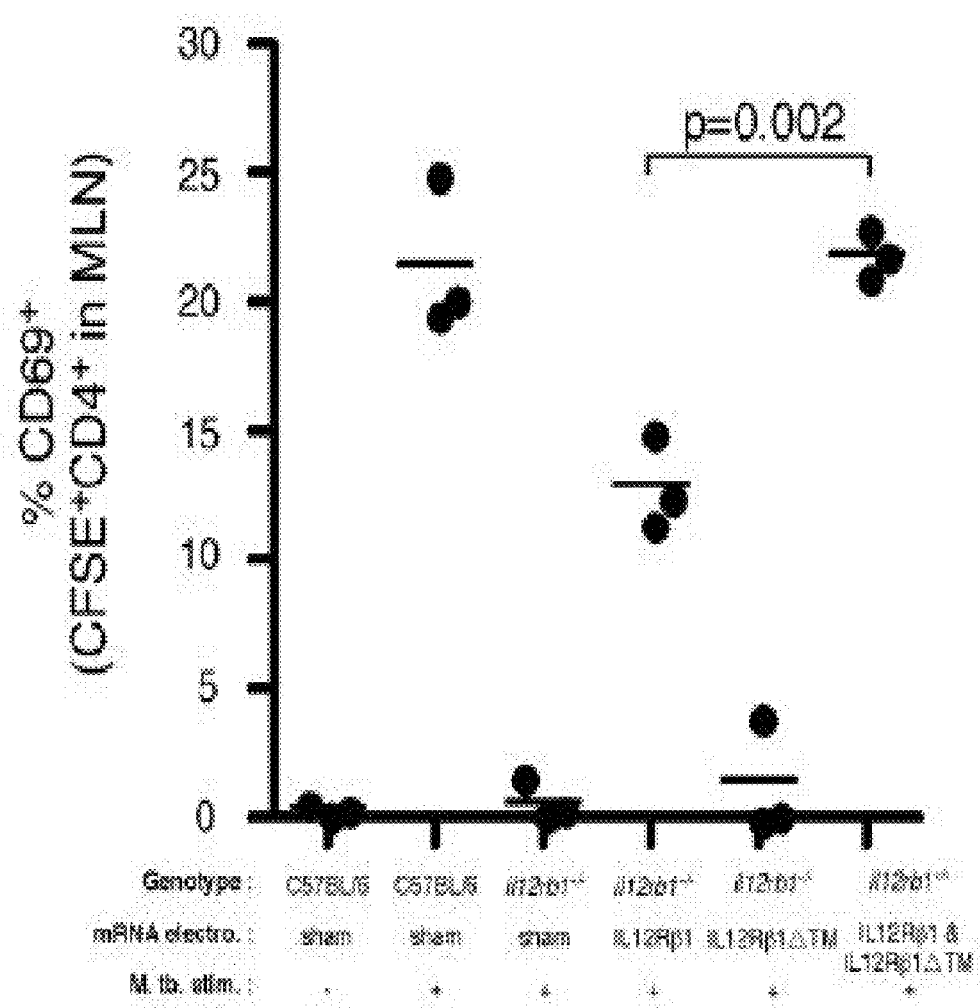

Finally, given that IL12Rβ1ΔTM enhanced IL12Rβ1-dependent DC migration in vitro, it was determined whether its expression in DCs accelerated the activation of *M. tuberculosis*-specific T cells in vivo. il12rb1$^{-/-}$ BMDCs were selectively restored with mRNAs for IL12Rβ1, IL12Rβ1ΔTM, or both IL12Rβ1 and IL12Rβ1ΔTM as described above. Following their electroporation and overnight culture, DCs were cultured with irradiated *M. tuberculosis* and ESAT$_{1-20}$ peptide for 3 hrs. After this period DCs were washed and instilled via the trachea into the lungs of C57BL/6 mice that had previously received 5×10$^6$ CFSE-labeled ESAT-TCR CD4$^+$ cells. Twelve hours after DC instillation the surface expression of CD44 and CD69 by CFSE$^+$ CD4$^+$ cells in the draining MLN was assessed by flow cytometry. As anticipated, mice that received sham electroporated DCs had fewer activated *M. tuberculosis*-specific T cells in the draining MLN relative to those that received sham electroporated C57BL/6 DCs (FIG. 12E). Restoration of IL12Rβ1 alone to il12rb1$^{-/-}$ DCs elevated the frequency of CD44$^{hi}$ and CD62L$^{lo}$ *M. tuberculosis*-specific T cells, however restoring IL12Rβ1ΔTM alone to il12rb1$^{-/-}$ DCs did not elevate the frequency of activated *M. tuberculosis*-specific T cells. Importantly, only when both IL12Rβ1 and IL12Rβ1ΔTM were restored to il12rb1$^{-/-}$ DCs did the frequency of activated *M. tuberculosis*-specific T cells return the level seen in mice that received C57BL/6 DCs. This result was observed across several independent experiments (FIG. 12F and FIG. 12G). These data demonstrate that IL12Rβ1ΔTM acts as a positive-regulator to enhance IL12Rβ1-dependent DC migration from the lung and IL12Rβ1-dependent activation of *M. tuberculosis*-specific T cells in the lung draining MLN.

i) IL12Rβ1ΔTM enhances other IL12Rβ1-dependent events

To determine whether IL12Rβ1ΔTM enhances other IL12Rβ1-dependent events an adapted STAT4-reporter assay developed by Visconti et al. was used. Following phosphorylation by IL12Rβ2 in an IL12-dependent manner, STAT4 translocates to the nucleus where it functions as a transcription factor for genes containing a gamma-activated sequence (i.e. GAS) promoter. In this assay NIH/3T3 cells are transiently transfected with plasmids that constitutively express IL12Rβ1, IL12Rβ2 and STAT4. STAT 4 phosphorylation is measured after addition of IL12 using a STAT4-reporter plasmid that contains firefly-luciferase under the GAS-promoter. Constitutively expressed *Renilla* luciferase is used to normalize for transfection efficiency. STAT4 activity was observed to be both IL12- and IL12Rβ1-dependent (FIG. 13b). When IL12Rβ1ΔTM is substituted for IL12Rβ1, STAT4 activation returns to media-alone levels. However co-transfection of IL12Rβ1ΔTM alongside IL12Rβ1 and IL12Rβ2 results in an approximate 30% increase in STAT4 activity. These results are statistically significant and have been observed across three independent experiments. Collectively these experiments suggest that IL12Rβ1ΔTM functions in transfected NIH/3T3 cells to enhance IL12Rβ1-dependent signaling.

V. Materials and Methods a) Mice

All mice were bred at the Trudeau Institute and were treated according to National Institutes of Health and Trudeau Institute Animal Care and Use Committee guidelines. C57BL/6, B6.129S1-Il12b$^{tm1jm}$/J (i.e. il12b$^{-/-}$ mice (Magram et al., 1996)), B6.129S1-Il12rb2$^{tm1jm}$/J (i.e. mice (Wu et al., 2000)), and B6.FVB-Tg (Itgax-DTR/eGFP)57Lan/J (i.e. CD11c-DTR) (Jung et al., 2002)) mice were originally purchased from Jackson Laboratory (Bar Harbor, Me.). C57BL/6 mice deficient of the B6.129S1-Il12rb2$^{tm1jm}$/J (il12rb1$^{-/-}$ mice) have been described (Wu et al., 1997) as have ESAT6$_{1-20}$ specific T cell receptor (TCR)-transgenic mice (Reiley et al., 2008).

b) Cell Preparations

*M. tuberculosis* infections were performed and the lung tissue and lymph nodes were processed as described previously (Khader et al., 2007). Single cell suspensions were prepared from either digested lung tissue or lymph nodes by direct dispersal through a 70-μm nylon tissue strainer (BD Falcon). The resultant suspension was treated with Geys solution (155 mM NH$_4$Cl, mM KHCO$_3$) to remove any residual red blood cells, washed twice with complete media, counted and stained for subsequent flow cytometric analysis.

c) Bone Marrow-Derived Dendritic Cells

BMDCs were generated from bone marrow of 4-5 week old C57BL/6 mice harvested via perfusion of the femur and tibia medullary cavities with ice cold DMEM. Marrow suspensions were pelleted and incubated in Geys solution to lyse red blood cells. The marrow was then resuspended at 4×10$^5$ cells/mL in complete supplemented DMEM (cDMEM). 5 mL of bone marrow homogenate was plated in a Petri dish (Corning Inc., Corning, N.Y.) along with 5 mL of 40 ng/mL recombinant murine GM-CSF (Peprotech, Rocky Hill, N.J.) in cDMEM solution for a final concentration of 20 ng/mL GM-CSF. Cultures were maintained at 37° C. and 10% CO$_2$ for 3 days, at which time an additional 10 mL of 20 ng/mL GM-CSF in cDMEM was added. At 6 days, non-adherent cells were collected and the presence of CD11c$^+$ cells confirmed by flow cytometric analysis. For indicated experiments CD11c$^+$ cells were positively selected by magnetic purification. In these cases 1×10$^6$ CD11c$^+$ cells were placed in a 2 mL culture with or without indicated concentrations of irradiated *M. tuberculosis, Y. pestis, M. avium*, TNFα, IL12 or IL12(p40)$_2$ in cDMEM for varying amounts of time at 37° C.

and 10% $CO_2$. After this period, cells were collected and either lysed for RNA and/or protein as indicated or used for chemotaxis measurements.

d) Flow Cytometry

All antibodies used for flow cytometric analysis were purchased from BD Pharmingen (San Diego, Calif., USA) or eBiosciences (San Diego, Calif., USA). Experimental cells were washed with FACS buffer (2% FCS in PBS), $F_c$ receptors were blocked using anti-CD16/CD32 (BD Pharmingen. Clone 2.4G2) for 15 minutes and cells were stained with antibodies that recognize CD11c (clone HL3), I-$A^b$ (clone AF6-120.1) and IL12Rβ1 (CD212, clone 114). For all surface markers, positive staining was established using appropriate isotype controls. Data were acquired using a FACSCalibur (BD Biosciences, San Jose, Calif.) and analyzed with FlowJo software (Tree Star Inc., Ashland, Oreg.).

e) In Vitro Chemotaxis Measurement

BMDCs were activated with indicated concentrations of irradiated *M. tuberculosis* and their ability to respond to the chemokine CCL19 (25 ng/mL; R&D Systems) was determined using the previously described in vitro transwell chemotaxis assay (Khader et al., 2006).

f) In Vivo Tracking of Lung CD11c$^+$ DCs

C57BL/6, il12b$^{-/-}$, il12rb1$^{-/-}$ and il12rb2$^{-/-}$ mice received a suspension of 5 µg of irradiated *M. tuberculosis* in a 5-mM CFSE (Invitrogen) solution delivered via the trachea. Eighteen hours after instillation, the draining MLN were harvested, and single cell suspensions were prepared. Flow cytometry was used to determine the frequency and total number of CFSE-labeled CD11c$^+$ cells that had accumulated within the MLN.

g) Bone-Marrow Chimeras

To generate mice in which only CD11c$^+$ cells were deficient of IL12Rβ1, mixed bone marrow chimeras were generated comprising irradiated C57BL/6 hosts reconstituted with 75% CD11c-DTR/25% il12rb1$^{-/-}$ bone marrow. Intraperitoneal (i.p.) injection of DT resuspended in sterile PBS theoretically removes CD11c$^+$ cells expressing the DTR leaving (in this case) only il12rb1$^{-/-}$ CD11c$^+$ cells. Briefly, 6-10 week old C57BL/6 hosts were lethally irradiated with 950 Rads (i.e. a split dose of 475 Rads each, four hours apart). The irradiated hosts then received 1×10$^7$ whole bone marrow donor cells comprising either 75% CD11c-DTR/25% il12rb1$^{-/-}$ bone marrow or 75% CD11c-DTR/25% C57BL/6 bone marrow as a control. Bone marrow was prepared as described above. Mice were allowed at least 6 weeks to reconstitute. Prior to ESAT$_{1-20}$/*M. tuberculosis* instillation, all mice received an i.p. injection of 4 ng DT/g of body mass to ablate DTR-transgenic CD11c$^+$ cells.

h) Cell Culture

For the generation of concanavalin-A blasts, C57BL/6 spleens were dispersed through a 70 µm nylon cell strainer (BD Biosciences, Bedford Mass.) and the cellular homogenate pelleted (270 g, 6 min at 4° C.) and resuspended in 2 mL of Geys solution to remove red blood cells. Splenocytes were washed and resuspended at 20×10$^6$ cells/mL in cDMEM and 1 mL of splenocytes was plated in 6-well dishes (Corning Inc., Corning, N.Y.) along with 1 mL of 10 µg/mL concanavalin-A in cDMEM solution (Sigma-Aldrich, St. Louis, Mo.) for a final concentration of 5 µg/mL concanavalin-A. Cultures were maintained at 37° C. and 10% $CO_2$ for 3 days before cells were harvested for RNA and/or protein as indicated.

i) RNA Purification and cDNA Synthesis

Total RNA was isolated from indicated tissues and/or cell populations using the RNeasy method (Qiagen) and was treated with DNAse (Ambion). cDNA was subsequently synthesized using SuperScript II reverse transcription PCR kit (Invitrogen) with random hexamer primers.

j) PCR

To amplify the IL12Rβ1 transcript primer pairs were used that selectively amplify the extracellular, transmembrane or intracellular encoding-portions. The relative positions of these primers (labeled P1-P6) are illustrated in FIG. 4B. P1-4 sequences are taken directly from a previous report of IL12Rβ1 expression in DCs (Grohmann et al., 1998). The 5 '-3' sequences of these and the other primers used in this study are as follows: P1 [SEQ ID NO: 3], TATGAGTGCTCCTG-GCAGTAT; P2 [SEQ ID NO: 4], GCCATGCTCCAAT-CACTCCAG; P3 [SEQ ID NO: 5], AATGTGCTCGC-CAAAACTCG; P4 [SEQ ID NO: 6], CGCAGTCTTATGGGTCCTCC; P5.[SEQ ID NO: 7], CTGCCTCTGCCTCTGAGTCT; P6 [SEQ ID NO: 8], GCCAATGTATCGAGACTGC. IL12Rβ1 transcripts were amplified by PCR in a 25-µl reaction comprising the following: 2.5 uL of a 10×PCR buffer (200 mM Tris pH 8.4, 500 mM KCl), 0.5 uL of 10 mM dNTPs, 1 uL 50 mM $MgCl_2$, 0.1 uL of 5 U/uL Taq polymerase (Invitrogen), 1 µL of 5 µM forward primer (P1 or P3), 1 uL of 5 uM reverse primer (P2, P4, P5 or P6), 17.9 uL of DNAse-free $H_2O$ and 1 uL of cDNA (a minimum of 200 pg cDNA). Following denaturation at 94° C. for 3 min, the reaction was cycled forty times under the following conditions: 94° C. for 45 seconds, 55° C. for 30 sec, 72° C. for 90 sec. The products of this reaction were either analyzed on a 2% agarose gel or kept for IL12Rβ1 Spectratype analysis as described below.

k) IL12Rβ1-Spectratype Analysis

IL12Rβ1-Spectratype analysis of IL12Rβ1 and IL12Rβ1ΔTM mRNAs—and the quantification of the resultant data—was a modification of the now commonly used TCR-CD3 Spectratype analysis (Pannetier et al., 1993). IL12Rβ1 and IL12Rβ1ΔTM cDNAs were first amplified by PCR in the 25-µl reaction detailed above with the forward primer 5'-GCAGCCGAGTGATGTACAAG-3' [SEQ 9] and reverse primer 5'-CTGCCTCTGCCTCTGAGTCT-3' [SEQ ID NO: 7]. The forward primer corresponds to nucleotides 1653-1672 of the mouse IL12Rβ1 transcript and precedes the transmembrane-encoding sequence (nucleotides 1739-1834). The reverse primer is downstream of the transmembrane-encoding sequence, corresponding to nucleotides 2067-2086 of the mouse IL12Rβ1 transcript. To fluorescently label the IL12Rβ1 and IL12Rβ1ΔTM amplicons a second runoff PCR reaction was performed as follows: 2.5 µl of the initial amplification reaction was added to 22.5 uL of a second PCR comprising 2.5 uL of 10×PCR buffer, 0.5 uL of 10 mM dNTPs, 1 uL 50 mM $MgCl_2$, 0.1 uL of 5 U/uL Taq polymerase (Invitrogen), 2.0 uL of a 5 uM FAM-labeled reverse primer (FAM-5'-AGTGCTGCCACAGGGTGTA-3'[SEQ ID NO: 10]), and 16.4 uL of DNAse-free $H_2O$ (final volume: 25 uL). Following denaturation at 94° C. for 5 min, the reaction was cycled four times under the following conditions: 95° C. for 2 minutes, 55° C. for 2 minutes, 72° C. for 20 minutes. 2.0 µL of the completed runoff PCR reaction was then added to 2.0 µl of ROX-500 size standard (Applied Biosystems) and 36 µl of HiDi Formamide (Applied Biosystems). Following denaturation, the products were detected and their size and relative amount determined using an Applied Biosystems 3100 sequencer analyzed with GeneScan software (Applied Biosystems). For calculating the ratio of IL12Rβ1ΔTM to IL12Rβ1 (i.e. IL12Rβ1ΔTM:IL12Rβ1) the area under the IL12Rβ1ΔTM peak was divided by the area under the reference IL12Rβ1 peak.

l) Plasmids and Transfections

Plasmids expressing IL12Rβ1 and IL12Rβ1ΔTM cDNAs in vector pEF-BOS (Mizushima and Nagata, 1990) under the EF1α promoter have been described (Chua et al., 1995) (pEF-BOS.IL12Rβ1 and pEF-BOS.IL12Rβ1ΔTM). pAcGFP1-N1 (Clontech Laboratories, Mountain View, Calif.) was used to express eGFP under the CMV promoter to identify transfected cells. For transfection into NIH/3T3 cells (ATCC, Manassas, Va.) the Polyfect system (Qiagen, Valencia, Calif.) was used as per the manufacturers instructions.

m) Western Blot Analysis

SDS-PAGE analysis of reduced protein samples and subsequent transfer to PVDF membrane was performed using standard protocols. Membranes were subsequently probed overnight with 400 ng/mL goat polyclonal anti-IL12Rβ1 (R&D Systems) in a solution of Tris-buffered saline (TBS) containing 2.5% powdered milk, washed with TBS, secondarily probed with HRP-conjugated anti-goat IgG and detected using ECL western blotting substrate (ThermoScientific, Rockford, Ill.) for chemiluminescence. For a positive control, recombinant mouse IL12Rβ1 (R&D Systems) was run simultaneously with each gel.

n) Determination of Total NFκB and Phospho-NFκB Levels

C57BL/6 and il12rb1$^{-/-}$ BMDCs were exposed to *M. tuberculosis* or media alone for indicated times. Following each time point, cells were collected and washed with ice-cold PBS. Cells were subsequently lysed by addition of ice-cold lysis buffer (20 mM Tris pH 7.5, 150 mM NaCl, 1 mM EDTA, 1 mM EGTA, 1% Triton X-100, 2.5 mM $Na_4P_2O_7$, 1 mM β-glycerophosphate, 1 mM $Na_3VO_4$, 1 ug/mL leupeptin plus 1 mM PMSF) and sonicated on ice. Total lysates were centrifuged at 14000 RPM for 10 minutes at 4° C.; the supernatants were aliquoted and stored at −80° C. until determination of total NFκB and phospho-NFκB levels by ELISA (PathScan Inflammation Multi-Target Sandwich ELISA; Cell Signaling Technology, Danvers, Mass.).

o) NFκB Electromobility Shift Assay (EMSA)

Nuclear extracts from indicated cell populations were subjected to polyacrylamide electrophoresis and EMSA analysis of subsequently generated blots with Panomics NFκB EMSA Kit (Fremont, Calif.) with biotinylated NFκB probe 5'-AGT-TGAGGGGACTTTCCCAGGC-3' [SEQ ID NO: 11] as per the manufacturers' instructions.

p) In Vitro mRNA Transcription

To generate in vitro transcribed (IVT) mRNA of IL12Rβ1, IL12Rβ1ΔTM and eGFP it was first necessary to subclone their respective cDNAs into a second plasmid downstream of a T7 phage polymerase. The IL12Rβ1 and IL12Rβ1ΔTM cDNAs were first amplified out of their pEF-BOS backbones using primers that flanked their start and stop codons; specifically 5'-TGTTTCTGAGCGTGGACAAG-3' [SEQ ID NO: 12] and 5'-CCGCAGTCTTATGGGTCCT-3' [SEQ ID NO: 13]. eGFP was amplified out of pAcGFP1-N1 using primers 5'-TAGCGCTACCGGACTCAGAT-3' [SEQ ID NO: 14] (cognate to the sequence just 5' of the eGFP start codon) and 5'-GGGAGGTGTGGGAGGTTTT-3' [SEQ ID NO: 15]. IL12Rβ1, IL12Rβ1ΔTM and eGFP amplicons were subsequently TA-cloned into pCR2.1 downstream of the T7 phage polymerase promoter to generate the plasmids pCR2.1.IL12Rβ1, pCR2.1.IL12Rβ1ΔTM and pCR2.1.eGFP, respectively. These constructs were subsequently used in the mMessage mMachine kit (Ambion) to generate 5' capped IVT mRNA as per the manufacturers instruction. mRNA quality was checked by gel electrophoresis and the concentration determined by spectrophotometric analysis at $OD_{260}$. mRNA aliquots were stored at −80° C. until use for transfections.

q) Electroporation of DCs

Electroporation of individual mRNAs into il12rb1$^{-/-}$ DCs was done as performed by Ponsaerts et al. (Ponsaerts et al., 2002) with minor modifications. Briefly, prior to electroporation, DCs were washed twice with electroporation buffer (Ambion) and resuspended to a final concentration of $5\times10^7$ cells/ml in electroporation buffer. 0.2 ml of the cell suspension was then mixed with 20 μg of IVT mRNA and electroporated in a 0.4 cm cuvette at 300 V and 150 μF using a Gene Pulser Xcell Electroporation System (BioRad). After electroporation, fresh complete medium was added to the cell suspension followed by incubation at 37° C. in a humidified atmosphere supplemented with 5% $CO_2$. For all electroporation experiments the co-transfection of eGFP-mRNA was used to both confirm transfection efficiency and to identify cells that were successfully transfected.

r) In Vivo Migration of Electroporated DCs

Following mRNA electroporation and overnight culture, $1\times10^6$ DCs were cultured with 10 μg/mL irradiated *M. tuberculosis* and 1 μM $ESAT_{1-20}$ peptide for 3 hrs. DCs were then washed, resuspended in PBS and instilled via the trachea into the lungs of Thy1.1 congenic mice. Eighteen hours prior to instillation each mouse had intravenously received $5\times10^6$ CFSE-labeled ESAT-TCR CD4$^+$ cells. The surface expression of CD44 and CD69 on CFSE$^+$CD4$^+$ cells in the draining MLNs was assessed 12 hours later by flow cytometry.

s) IL12Rβ1 Isoform Expression by Human DCs

Monocyte-derived DCs were generated by incubating CD14$^+$ monocytes (magnetically purified from apheresis samples) with GMCSF (20 ng/ml, Peprotech) and IL4 (50 ng/ml, R&D) for 7 days. DCs were then incubated for 24 h with LPS (1 μg/ml) or for 3 days with either of the following: IL1β (10 ng/ml), IL10 (200 ng/ml), IL6 (10 ng/ml), IL2 (20 U/ml), CCL3 (50 ng/ml), PlGF (50 ng/ml) or RPMI media (control). Alternatively, DCs were stimulated with *M. tuberculosis* over a 6-hour period. cDNA generated from these populations was then amplified with primer pairs that either amplified both IL12Rβ1 isoforms 1 and 2 (Common; 5'-ACACTCTGGGTGGAATCCTG-3' [Forward] [SEQ ID NO: 1] and 5'GCCAACTTGGACACCTTGAT-3' [Reverse] [SEQ ID NO: 2]), only isoform 1 (Isoform 1 Specific; 5'-ACACTCTGGGTGGAATCCTG-3' [Forward] [SEQ ID NO: 1] and 5'CACCCTCTCTGAGCCTCAAC-3' [Reverse] [SEQ ID NO: 16] or only isoform 2 (Isoform 2 Specific; 5'-ACACTCTGGGTGGAATCCTG-3' [Forward] [SEQ ID NO: 1] and 5'CTAGCACTTTGGGAGGTGGA-3' [Reverse] [SEQ ID NO: 17]). The conditions used to amplify with these primers were the same as those used for the primary PCR of IL12Rβ1 Spectratype analysis detailed above. cDNA from CD3$^+$ PBMCs was used as a positive control for IL12Rβ1 expression. Amplicons were analyzed by 2% agarose gel electrophoresis.

t) Statistical Analysis

Differences between the means of experimental groups were analyzed with the two-tailed Student's t-test as the data was considered parametric. Differences with a P value of 0.05 or less were considered significant. Prism software was used for all analyses.

We claim:

1. A method for detecting a transcript and a splice variant thereof, comprising:
   a) providing:
      i) a sample comprising cDNA molecules corresponding to the transcript encoding IL12Rβ1 isoform 1 and the splice variant encoding IL12Rβ1 isoform 2, at least one of said cDNA molecules not comprising a transmembrane-encoding region,
      ii) a PCR primer set flanking said transmembrane-encoding region of said cDNA molecules, and
   b) amplifying said cDNA with said PCR primer set so as to produce PCR products, and
   c) detecting the PCR products corresponding to the cDNA molecules of said transcript encoding IL12Rβ1 isoform 1 and said splice variant encoding IL12Rβ1 isoform 2.

2. The method of claim 1, wherein said detecting is performed with a fluorescent-conjugated primer or probe.

3. The method of claim 1, wherein said detecting is performed by fluorescent capillary electrophoresis.

4. The method of claim 3, wherein said fluorescent capillary electrophoresis produces first and second peaks corresponding to the labeled PCR products of the cDNA molecules of said transcript encoding IL12Rβ1 isoform 1 and said splice variant encoding IL12Rβ1 isoform 2.

5. The method of claim 4, wherein the relative abundance of each of said peaks is determined.

6. The method of claim 1, wherein the nucleotide sequence of the forward PCR primer is SEQ ID NO:1.

7. The method of claim 1, wherein the nucleotide sequence of the reverse PCR primer is SEQ ID NO:2.

8. The method of claim 1, wherein detecting the PCR products further comprises detecting the ratio of the PCR products corresponding to the cDNA molecules of said transcript encoding IL12Rβ1 isoform 1 and the splice variant encoding IL12Rβ1 isoform 2.

9. The method of claim 1, wherein said sample is isolated from a cell.

10. The method of claim 9, wherein said cell is a dendritic cell.

11. The method of claim 10, wherein said cell has been exposed to a pathogen.

12. The method of claim 11, wherein said pathogen is *Mycobacterium tuberculosis*.

13. A primer consisting of the nucleotide sequence of SEQ ID NO: 1.

14. A primer set comprising the primer of claim 13 and a second primer consisting of the nucleotide sequence of SEQ ID NO: 2.

15. A kit comprising the primer set of claim 14.

* * * * *

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
acactctggg tggaatcctg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gccaacttgg acaccttgat                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tatgagtgct cctggcagta t                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gccatgctcc aatcactcca g                                             21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
aatgtgctcg ccaaaactcg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
cgcagtctta tgggtcctcc                                               20

<210> SEQ ID NO 7
<211> LENGTH: 20
<212> TYPE: DNA

```
<213> ORGANISM: Artificial Sequence
<220> FEATURE:
<223> OTHER INFORMATION: Synthetic

<400> SEQUENCE: 7
ctgcctctgc ctctgagtct                                              20

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gccaatgtat cgagactgc                                               19

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gcagccgagt gatgtacaag                                              20

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
agtgctgcca cagggtgta                                               19

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
agttgagggg actttcccag gc                                           22

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tgtttctgag cgtggacaag                                              20

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
ccgcagtctt atgggtcct                                               19
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tagcgctacc ggactcagat                                               20

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
gggaggtgtg ggaggtttt                                                19

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
caccctctct gagcctcaac                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ctagcacttt gggaggtgga                                               20

<210> SEQ ID NO 18
<211> LENGTH: 4
<212> TYPE: PRT
<213> ORGANISM: Mus musculus

<400> SEQUENCE: 18

Arg Phe Ser Phe
1

<210> SEQ ID NO 19
<211> LENGTH: 5
<212> TYPE: PRT
<213> ORGANISM: Mus musculus

<400> SEQUENCE: 19

Arg Ala Ala Trp His
1               5

<210> SEQ ID NO 20
<211> LENGTH: 24
<212> TYPE: DNA
<213> ORGANISM: Mus musculus

<400> SEQUENCE: 20
cgctttagct ttgaggtgca gatt                                          24
```

```
<210> SEQ ID NO 21
<211> LENGTH: 27
<212> TYPE: DNA
<213> ORGANISM: Mus musculus

<400> SEQUENCE: 21
attggcttaa acagggccgc ctggcac                                             27

<210> SEQ ID NO 22
<211> LENGTH: 27
<212> TYPE: DNA
<213> ORGANISM: Mus musculus

<400> SEQUENCE: 22
cgctttagct ttgggccgcc tggcact                                             27

<210> SEQ ID NO 23
<211> LENGTH: 9
<212> TYPE: PRT
<213> ORGANISM: Mus musculus

<400> SEQUENCE: 23

Arg Phe Ser Phe Gly Pro Pro Gly Thr
1               5

<210> SEQ ID NO 24
<211> LENGTH: 659
<212> TYPE: PRT
<213> ORGANISM: Homo sapiens

<400> SEQUENCE: 24

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
                20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp
        50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
                100                 105                 110

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
        130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
                180                 185                 190

Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
        210                 215                 220
```

-continued

```
Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
            245                 250                 255

Thr Leu Lys Glu Gln Pro Thr Gln Leu Glu Leu Pro Glu Gly Cys Gln
        260                 265                 270

Gly Leu Ala Pro Gly Thr Glu Val Thr Tyr Arg Leu Gln Leu His Met
    275                 280                 285

Leu Ser Cys Pro Cys Lys Ala Lys Ala Thr Arg Thr Leu His Leu Gly
290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
            325                 330                 335

Asp Thr His Thr Glu Pro Val Ala Leu Asn Ile Ser Val Gly Thr Asn
        340                 345                 350

Gly Thr Thr Met Tyr Trp Pro Ala Arg Ala Gln Ser Met Thr Tyr Cys
    355                 360                 365

Ile Glu Trp Gln Pro Val Gly Gln Asp Gly Gly Leu Ala Thr Cys Ser
370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
            405                 410                 415

Thr Ile Phe Ala Ser Ala His Pro Glu Lys Leu Thr Leu Trp Ser Thr
        420                 425                 430

Val Leu Ser Thr Tyr His Phe Gly Gly Asn Ala Ser Ala Ala Gly Thr
    435                 440                 445

Pro His His Val Ser Val Lys Asn His Ser Leu Asp Ser Val Ser Val
450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu Pro
            485                 490                 495

Val Gln Pro Thr Glu Thr Gln Val Thr Leu Ser Gly Leu Arg Ala Gly
        500                 505                 510

Val Ala Tyr Thr Val Gln Val Arg Ala Asp Thr Ala Trp Leu Arg Gly
    515                 520                 525

Val Trp Ser Gln Pro Gln Arg Phe Ser Ile Glu Val Gln Val Ser Asp
530                 535                 540

Trp Leu Ile Phe Phe Ala Ser Leu Gly Ser Phe Leu Ser Ile Leu Leu
545                 550                 555                 560

Val Gly Val Leu Gly Tyr Leu Gly Leu Asn Arg Ala Ala Arg His Leu
            565                 570                 575

Cys Pro Pro Leu Pro Thr Pro Cys Ala Ser Ser Ala Ile Glu Phe Pro
        580                 585                 590

Gly Gly Lys Glu Thr Trp Gln Trp Ile Asn Pro Val Asp Phe Gln Glu
    595                 600                 605

Glu Ala Ser Leu Gln Glu Ala Leu Val Val Glu Met Ser Trp Asp Lys
610                 615                 620

Gly Glu Arg Thr Glu Pro Leu Glu Lys Thr Glu Leu Pro Glu Gly Ala
625                 630                 635                 640

Pro Glu Leu Ala Leu Asp Thr Glu Leu Ser Leu Glu Asp Gly Asp Arg
```

Cys Lys Ala

<210> SEQ ID NO 25
<211> LENGTH: 381
<212> TYPE: PRT
<213> ORGANISM: Homo sapiens

<400> SEQUENCE: 25

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Asp Gly Met Ile Ser Ala His Cys Asn Leu Arg Leu
            340                 345                 350

Pro Asp Ser Arg Asp Ser Pro Ala Ser Ala Ser Arg Val Ala Gly Ile
        355                 360                 365

```
Thr Gly Ile Cys His His Thr Arg Leu Ile Leu Tyr Phe
    370                 375                 380
```